United States Patent
Eggers et al.

(10) Patent No.: US 6,228,078 B1
(45) Date of Patent: May 8, 2001

(54) METHODS FOR ELECTROSURGICAL DERMATOLOGICAL TREATMENT

(75) Inventors: Philip E. Eggers, Dublin, OH (US); Hira V. Thapliyal, Los Altos, CA (US)

(73) Assignee: ArthroCare Corporation, Sunnyvale, CA (US)

( * ) Notice: Subject to any disclaimer, the term of this patent is extended or adjusted under 35 U.S.C. 154(b) by 0 days.

(21) Appl. No.: 08/978,340

(22) Filed: Nov. 25, 1997

Related U.S. Application Data

(63) Continuation-in-part of application No. 08/562,332, filed on Nov. 22, 1995, now Pat. No. 6,024,733.

(51) Int. Cl.⁷ .................................................. A61B 18/14
(52) U.S. Cl. ............................... 606/32; 606/41; 606/50; 607/99; 604/114
(58) Field of Search .................................. 606/32, 41, 49, 606/50; 607/98, 99, 101, 105; 604/114

(56) References Cited

U.S. PATENT DOCUMENTS

| | | |
|---|---|---|
| 2,050,904 | 8/1936 | Trice . |
| 4,033,351 | 7/1977 | Hetzel ................................ 128/303 |
| 4,040,426 | 8/1977 | Morrison, Jr. ...................... 128/303 |
| 4,043,342 | 8/1977 | Morrison, Jr. ...................... 128/303 |
| 4,116,198 | 9/1978 | Roos .................................. 128/303 |
| 4,184,492 | 1/1980 | Meinke et al. ...................... 128/303 |
| 4,202,337 | 5/1980 | Hren et al. .......................... 128/303 |
| 4,228,800 | 10/1980 | Degler, Jr. et al. ................. 128/303 |
| 4,248,231 | 2/1981 | Herczog et al. .................... 128/303 |
| 4,326,529 | 4/1982 | Doss ................................. 128/303.1 |
| 4,381,007 | 4/1983 | Doss ................................. 128/303.1 |
| 4,476,862 | 10/1984 | Pao ................................. 128/303.17 |
| 4,532,924 | 8/1985 | Auth et al. .......................... 128/303 |
| 4,548,207 | 10/1985 | Reimels ............................. 128/303 |
| 4,567,890 | 2/1986 | Ohta et al. ...................... 128/303.13 |

(List continued on next page.)

FOREIGN PATENT DOCUMENTS

| | | | |
|---|---|---|---|
| 44 25 015 | 1/1996 | (DE) | .............................. A61B/17/39 |
| 515 867 | 12/1992 | (EP) | .............................. A61B/17/36 |
| 0 597 463 | 5/1994 | (EP) | . |
| 0 703 461 A2 | 3/1996 | (EP) | .............................. G01R/27/02 |
| 0 740 926 | 11/1996 | (EP) | .............................. A61B/17/39 |
| 0 754 437 | 1/1997 | (EP) | .............................. A61B/17/39 |

(List continued on next page.)

OTHER PUBLICATIONS

P.C. Nardella (1989) *SPIE* 1068:42–49 Radio Frequency Energy and Impedence Feedback.

Rand et al. (1985) *J. Arthro. Surg.* 1:242–246 Effect of Electrocautery on Fresh Human Articular Cartilage.

(List continued on next page.)

*Primary Examiner*—Lee Cohen
(74) *Attorney, Agent, or Firm*—John T. Raffle

(57) ABSTRACT

Systems and methods are provided for selectively applying electrical energy to a target location on an external body surface, such as skin tissue removal and/or collagen shrinkage in the epidermis or dermis, e.g., the removal of pigmentations, vascular lesions (e.g., leg veins), scars, tattoos, etc., and for other surgical procedures on the skin, such as tissue rejuvenation, cosmetic surgery, wrinkle removal, hair removal and/or transplant procedures. The present invention applies high frequency (RF) electrical energy to one or more electrode terminals adjacent an external body surface, such as the outer surface of the skin, to remove and/or modify the structure of tissue structures within the skin. Depending on the specific cosmetic procedure, the present invention may be used to: (1) volumetrically remove tissue or hair (i.e., ablate or effect molecular dissociation of the tissue structure); (2) separate a tissue layer from an underlying tissue layer so that the tissue layer can be removed; (3) shrink or contract collagen connective tissue; and/or (4) coagulate blood vessels underlying the surface of the skin.

43 Claims, 18 Drawing Sheets

U.S. PATENT DOCUMENTS

| | | | |
|---|---|---|---|
| 4,593,691 | 6/1986 | Lindstrom et al. | 128/303.14 |
| 4,658,817 | 4/1987 | Hardy | 128/303 |
| 4,674,499 | 6/1987 | Pao | 128/303 |
| 4,682,596 | 7/1987 | Bales et al. | 128/303 |
| 4,706,667 | 11/1987 | Roos | 128/303 |
| 4,736,743 | 4/1988 | Daikuzono | 128/303.1 |
| 4,737,678 | 4/1988 | Hasegawa | 313/36 |
| 4,762,128 | 8/1988 | Rosenbluth | 128/343 |
| 4,765,331 | 8/1988 | Petruzzi et al. | 128/303 |
| 4,785,806 | 11/1988 | Deckelbaum | 128/303.1 |
| 4,799,480 | 1/1989 | Abraham et al. | 128/303 |
| 4,823,791 | 4/1989 | D'amelio | 123/303 |
| 4,860,752 | 8/1989 | Turner | 128/422 |
| 4,931,047 | 6/1990 | Broadwin et al. | 604/22 |
| 4,936,301 | 6/1990 | Rexroth et al. | 606/45 |
| 4,943,290 | 7/1990 | Rexroth et al. | 606/45 |
| 4,955,377 | 9/1990 | Lennox et al. | 128/401 |
| 4,967,765 | 11/1990 | Turner et al. | 128/785 |
| 4,968,314 | 11/1990 | Michaels | 606/7 |
| 4,976,711 | 12/1990 | Parins et al. | 606/48 |
| 4,979,948 | 12/1990 | Geddes et al. | 606/33 |
| 4,998,933 | 3/1991 | Eggers et al. | 606/41 |
| 5,007,437 | 4/1991 | Sterzer | 428/786 |
| 5,007,908 | 4/1991 | Rydell | 606/47 |
| 5,009,656 | 4/1991 | Reimels | 606/48 |
| 5,035,696 | 7/1991 | Rydell | 606/47 |
| 5,037,421 | 8/1991 | Boutacoff et al. | 606/15 |
| 5,057,105 | 10/1991 | Malone et al. | 606/28 |
| 5,057,106 | 10/1991 | Kasevich et al. | 606/33 |
| 5,059,192 | 10/1991 | Zaias | 606/9 |
| 5,061,266 | 10/1991 | Hakky | 606/15 |
| 5,065,515 | 11/1991 | Iderosa | 30/140 |
| 5,078,717 | 1/1992 | Parins et al. | 606/48 |
| 5,080,660 | 1/1992 | Buelna | 606/41 |
| 5,083,565 | 1/1992 | Parins | 128/642 |
| 5,098,431 | 3/1992 | Rydell | 606/48 |
| 5,102,410 | 4/1992 | Dressel | 606/15 |
| 5,108,391 | 4/1992 | Flachenecker et al. | 606/38 |
| 5,112,330 | 5/1992 | Nishigaki et al. | 606/46 |
| 5,122,138 | 6/1992 | Manwaring | 606/46 |
| 5,125,928 | 6/1992 | Parins et al. | 606/48 |
| 5,147,354 | 9/1992 | Boutacoff et al. | 606/15 |
| 5,178,620 | 1/1993 | Eggers et al. | 606/41 |
| 5,182,857 | 2/1993 | Simon | 30/34 |
| 5,190,517 | 3/1993 | Zieve et al. | 604/22 |
| 5,192,280 | 3/1993 | Parins | 606/48 |
| 5,195,959 | 3/1993 | Smith | 604/34 |
| 5,197,963 | 3/1993 | Parins | 606/46 |
| 5,217,455 | 6/1993 | Tan | 606/9 |
| 5,217,457 | 6/1993 | Delahuerga et al. | 606/42 |
| 5,226,907 | 7/1993 | Tankovich | 606/133 |
| 5,231,984 | 8/1993 | Santana-Blank | 128/395 |
| 5,241,972 | 9/1993 | Bonati | 128/898 |
| 5,249,585 | 10/1993 | Turner et al. | 607/99 |
| 5,261,410 | 11/1993 | Alfano et al. | 128/664 |
| 5,267,994 | 12/1993 | Gentelia et al. | 606/15 |
| 5,267,997 | 12/1993 | Farin et al. | 606/38 |
| 5,273,524 | 12/1993 | Fox et al. | 604/21 |
| 5,277,201 | 1/1994 | Stern | 607/98 |
| 5,281,216 | 1/1994 | Klicek | 606/42 |
| 5,281,218 | 1/1994 | Imran | 606/41 |
| 5,287,380 | 2/1994 | Hsia | 372/69 |
| 5,290,273 | 3/1994 | Tan | 606/9 |
| 5,290,282 | 3/1994 | Casscells | 606/29 |
| 5,300,069 | 4/1994 | Hunsberger et al. | 606/37 |
| 5,300,099 | 4/1994 | Rudie | 607/101 |
| 5,301,687 | 4/1994 | Wong et al. | 607/116 |
| 5,304,169 | 4/1994 | Sand | 606/5 |
| 5,304,170 | 4/1994 | Green | 606/9 |
| 5,312,395 | 5/1994 | Tan et al. | 606/9 |
| 5,312,400 | 5/1994 | Bales et al. | 606/41 |
| 5,314,406 | 5/1994 | Arias et al. | 604/21 |
| 5,320,618 | 6/1994 | Gustafsson | 606/9 |
| 5,322,507 | 6/1994 | Costello et al. | 128/4 |
| 5,324,254 | 6/1994 | Phillips | 604/21 |
| 5,326,343 | 7/1994 | Rudie et al. | 607/101 |
| 5,329,943 | 7/1994 | Johnson | 128/898 |
| 5,330,470 | 7/1994 | Hagen | 606/42 |
| 5,330,518 | 7/1994 | Neilson et al. | 607/101 |
| 5,334,140 | 8/1994 | Phillips | 604/35 |
| 5,334,183 | 8/1994 | Wuchinich | 606/46 |
| 5,336,217 | 8/1994 | Buys et al. | 606/9 |
| 5,336,220 | 8/1994 | Ryan et al. | 604/22 |
| 5,342,357 | 8/1994 | Nardella | 606/40 |
| 5,360,447 | 11/1994 | Koop | 623/15 |
| 5,366,443 | 11/1994 | Eggers et al. | 606/114 |
| 5,370,642 | 12/1994 | Keller | 606/9 |
| 5,370,675 | 12/1994 | Edwards et al. | 607/101 |
| 5,380,277 | 1/1995 | Phillips | 604/33 |
| 5,380,316 | 1/1995 | Aita et al. | 606/7 |
| 5,383,876 | 1/1995 | Nardella | 606/49 |
| 5,383,917 | 1/1995 | Desai et al. | 607/702 |
| 5,389,096 | 2/1995 | Aita et al. | 606/15 |
| 5,395,312 | 3/1995 | Desai | 604/22 |
| 5,417,687 | 5/1995 | Nardella et al. | 606/32 |
| 5,419,767 | 5/1995 | Eggers et al. | 604/114 |
| 5,423,803 | 6/1995 | Tankovich | 606/9 |
| 5,425,728 | 6/1995 | Tankovich | 606/9 |
| 5,433,708 | 7/1995 | Nichols et al. | 604/113 |
| 5,441,499 | 8/1995 | Fritzsch | 606/45 |
| 5,445,634 | 8/1995 | Keller | 606/9 |
| 5,454,809 | 10/1995 | Janssen | 606/41 |
| 5,484,435 | 1/1996 | Fleenor et al. | 606/46 |
| 5,490,850 | 2/1996 | Ellman et al. | 606/45 |
| 5,514,130 | 5/1996 | Baker | 606/41 |
| 5,522,813 | 6/1996 | Trellas | 606/2 |
| 5,556,397 | 9/1996 | Long et al. | 606/48 |
| 5,569,242 | 10/1996 | Lax et al. | 606/42 |
| 5,578,029 | 11/1996 | Trellas et al. | 606/25 |
| 5,584,872 | 12/1996 | LaFontaine et al. | 607/116 |
| 5,609,151 | 3/1997 | Mulier et al. | 128/642 |
| 5,660,836 | 8/1997 | Knowlton | 424/400 |
| 5,676,693 | 10/1997 | LaFontaine et al. | 607/116 |
| 5,681,282 | 10/1997 | Eggers et al. | 604/114 |
| 5,683,366 | 11/1997 | Eggers et al. | 604/114 |
| 5,683,386 | 11/1997 | Ellman et al. | 606/41 |
| 5,683,387 | 11/1997 | Garito et al. | 606/45 |
| 5,695,495 | 12/1997 | Ellman et al. | 606/41 |
| 5,697,281 | 12/1997 | Eggers et al. | 604/114 |
| 5,697,536 | 12/1997 | Eggers et al. | 604/114 |
| 5,697,882 | 12/1997 | Eggers et al. | 604/114 |
| 5,697,909 | 12/1997 | Eggers et al. | 604/114 |
| 5,700,262 | 12/1997 | Acosta et al. | 606/48 |
| 5,725,524 | 3/1998 | Mulier et al. | 606/41 |
| 5,746,746 | 5/1998 | Garito et al. | 606/41 |
| 5,749,869 | 5/1998 | Lindenmeier et al. | 606/34 |
| 5,755,753 | * 5/1998 | Knowlton | 607/98 |
| 5,766,153 | 6/1998 | Eggers et al. | 604/114 |
| 5,807,395 | 9/1998 | Mulier et al. | 606/41 |
| 5,810,764 | 9/1998 | Eggers et al. | 604/23 |
| 5,843,019 | 12/1998 | Eggers et al. | 604/22 |
| 5,843,078 | 12/1998 | Sharkey . | |
| 5,860,951 | 1/1999 | Eggers et al. | 604/49 |
| 5,871,469 | 2/1999 | Eggers et al. | 604/114 |
| 5,873,855 | 2/1999 | Eggers et al. | 604/114 |
| 5,888,198 | 3/1999 | Eggers et al. | 604/114 |
| 5,891,095 | 4/1999 | Eggers et al. | 604/114 |
| 5,897,553 | 4/1999 | Mulier et al. | 606/41 |
| 5,902,272 | 5/1999 | Eggers et al. | 604/114 |
| 5,944,715 | 8/1999 | Goble et al. | 606/41 |

FOREIGN PATENT DOCUMENTS

| | | | |
|---|---|---|---|
| 2308979 | 7/1997 | (GB) | A61B/17/39 |
| 2308980 | 7/1997 | (GB) | A61B/17/36 |
| 2308981 | 7/1997 | (GB) | A61B/17/39 |
| 57-117843 | 7/1982 | (JP) | A61B/17/39 |
| WO 90/07303 | 7/1990 | (WO) | A61B/17/39 |
| WO 91/13650 | 9/1991 | (WO) . | |
| WO 92/21278 | 12/1992 | (WO) | A61B/5/04 |
| WO 93/13816 | 7/1993 | (WO) | A61B/17/36 |
| 93/20747 | 10/1993 | (WO) | A61B/5/00 |
| WO 94/04220 | 3/1994 | (WO) . | |
| 94/08654 | 4/1994 | (WO) | A61M/37/00 |
| WO 94/14383 | 7/1994 | (WO) | A61B/17/36 |
| WO 94/26228 | 11/1994 | (WO) . | |
| 95/34259 | 12/1995 | (WO) | A61F/5/48 |
| 96/00042 | 1/1996 | (WO) | A61B/17/39 |
| 98/07468 | 8/1996 | (WO) . | |
| 96/34568 | 11/1996 | (WO) . | |
| 97/00646 | 1/1997 | (WO) | A61B/17/39 |
| 97/00647 | 1/1997 | (WO) | A61B/17/39 |
| 97/15238 | 5/1997 | (WO) | A61B/17/39 |
| 97/24073 | 7/1997 | (WO) | A61B/17/39 |
| 97/24992 | 7/1997 | (WO) | A61B/17/38 |
| 97/24993 | 7/1997 | (WO) | A61B/17/39 |
| 97/24994 | 7/1997 | (WO) | A61B/17/39 |
| 97/48346 | 12/1997 | (WO) | A61B/17/39 |
| 98/11944 | 3/1998 | (WO) | A61N/5/02 |
| 98/27879 | 7/1998 | (WO) | A61B/17/36 |

OTHER PUBLICATIONS

V.E. Elsasser et al. *Acta Medicotechnica* vol. 24, No. 4, pp. 129–134 (1976).

E. V. Kramolowsky et al. *J. of Urology* vol. 143, pp. 275–277 (1990).

J. W. Ramsey et al. *Urologicl Research* vol. 13, pp. 99–102 (1985).

R. Tucker et al., Abstract P14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

E. Kramolowsky et al. (1991) *J. of Urology* 146:669–674.

J. Pearce *Electrosurgery*, (1986) John Wiley & Sons, New York, pp. 17, 69–75 and 87.

Slager et al. (1985) *JACC* 5 (6): 1382–6.

Slager et al. (1987) *Z. Kardiol.* 76:Suppl. 6, 67–71.

Buchelt, M. et al. "Excimer Laser Ablation of Fibrocartilage: An In Vitro and In Vivo Study," (1991) Lasers in Surgery and Medicine 11:271–279.

Costello, A. J. et al. "Nd:YAG Laser Ablation of the Prostate as a Treatment of Benign Prostatic Hypertrophy," (1992) Lasers in Surger and Medicine 12:121–124.

\* cited by examiner

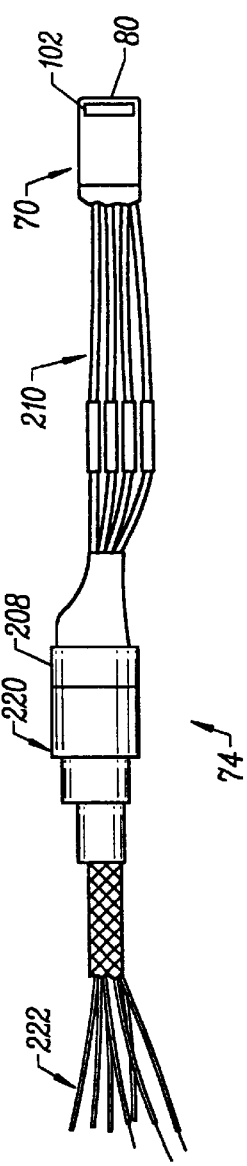
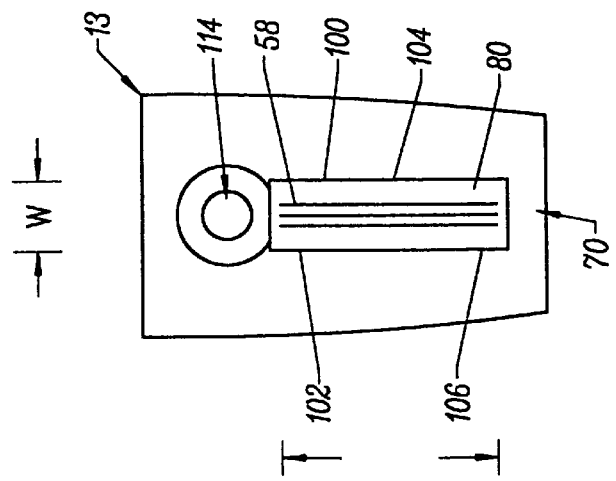
FIG. 5
FIG. 4

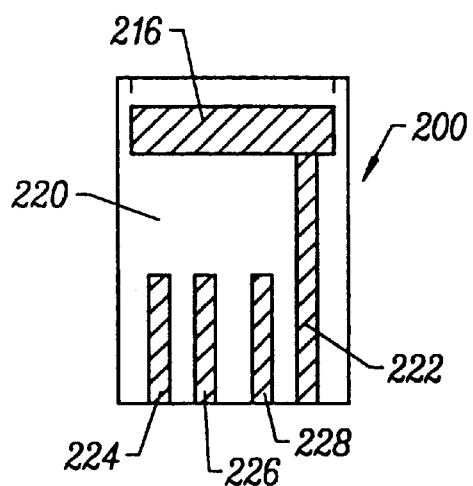
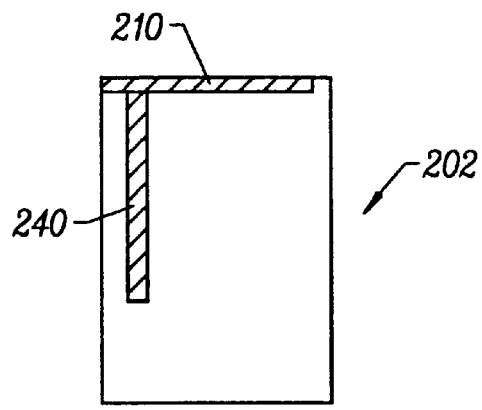
FIG. 9A
FIG. 10A
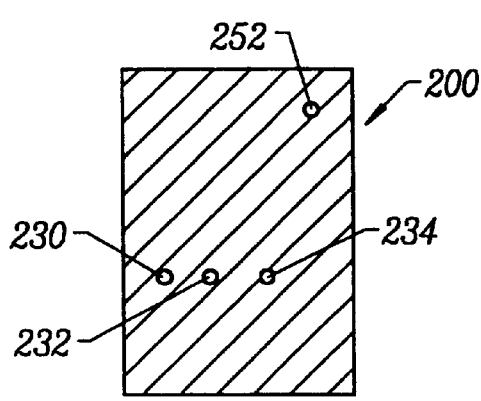
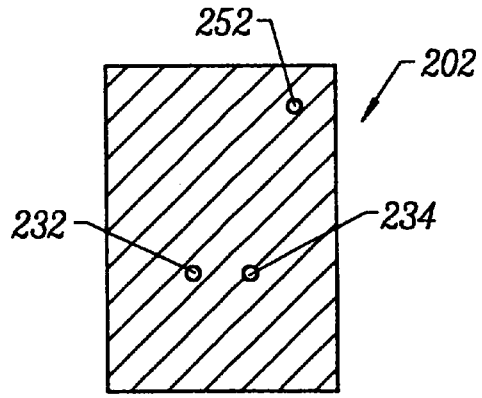
FIG. 9B
FIG. 10B

METHODS FOR ELECTROSURGICAL DERMATOLOGICAL TREATMENT

RELATED APPLICATIONS

The present invention is a continuation-in-part of U.S. patent application Ser. No. 08/562,332, filed Nov. 22, 1995, now U.S. Pat. No. 6,024,733, entitled "System and Method for Epidermal Tissue Ablation", the complete disclosure of which is incorporated herein by reference for all purposes.

The present invention is related to commonly assigned co-pending Provisional patent applications entitled "SYSTEMS AND METHODS FOR ELECTROSURGICAL TISSUE AND FLUID COAGULATION" and "SYSTEMS AND METHODS FOR ELECTROSURGICAL TISSUE RESECTION AND ABLATION", filed on Oct. 23, 1997, Ser. Nos. 60/062,996 and 60/062,997, non-provisional patent application Ser. No. 08/942,580, filed on Oct. 2, 1997, entitled "SYSTEMS AND METHODS FOR ELECTROSURGICAL TISSUE CONTRACTION", U.S. application Ser. No. 08/753227, filed on Nov. 22, 1996, U.S. application Ser. No. 08/687792, filed on Jul. 18, 1996, and PCT International Application, U.S. National Phase Ser. No. PCT/US94/05168, filed on May 10, 1994, which was a continuation-in-part of application Ser. No. 08/059,681, filed on May 10, 1993, which was a continuation-in-part of application Ser. No. 07/958,977, filed on Oct. 9, 1992 which was a continuation-in-part of application Ser. No. 07/817,575, filed on Jan. 7, 1992, the complete disclosures of which are incorporated herein by reference for all purposes. The present invention is also related to commonly assigned U.S. Pat. No. 5,683,366, filed Nov. 22, 1995 and patent application Ser. No. 08/485,219, filed on Jun. 7, 1995, the complete disclosures of which are incorporated herein by reference for all purposes.

BACKGROUND OF THE INVENTION

The present invention relates generally to the field of electrosurgery, and more particularly to surgical devices and methods which employ high frequency electrical energy to treat a patient's skin, including skin resurfacing procedures, the removal of pigmentations, vascular lesions, scars and tattoos, hair removal and/or transplant procedures, treatment of skin cancer, skin rejuvenation (e.g., wrinkle removal) and the like.

In early dermatology procedures, cosmetic surgeons often employed chemical peels and/or dermabrasion techniques to remove outer layers of the patient's skin to rejuvenate wrinkled skin or to remove skins disorders, such as acne, lesions, early skin cancer, etc. These dermabrasion and chemical procedures, however, are difficult to control, requiring great surgical skill. In addition, these somewhat inelegant techniques often cause excessive bleeding, collateral tissue damage and patient discomfort.

In an effort to overcome some of the limitations of dermabrasion and chemical peels, lasers have been developed for use in cosmetic surgery. Lasers have improved the accuracy of skin resurfacing procedures, and they have reduced collateral damage to the tissue surrounding and underlying the treatment site. In laser dermatology applications, a handpiece is typically used to guide the output of a laser to the patient's skin, and to form a laser spot of a desired size on the region of the skin which is to be treated. The handpiece is typically attached to one end of an articulated arm which transmits the output of a medical laser (such as $CO_2$ or Er: YAG lasers) to the handpiece and allows the handpiece a wide range of motion.

Although initially promising, lasers suffer from a number of drawbacks in dermatology procedures. In the first place, laser equipment can be very expensive because of the costs associated with the laser light sources. Moreover, those lasers which permit acceptable depths of necrosis (such as excimer lasers, erbium:YAG lasers, and the like) provide a very low volumetric ablation rate, requiring numerous passes over the same treatment area which amounts to longer procedural times. In addition, erbium:YAG lasers generally do not provide effective hemostasis during the procedure, resulting in excessive bleeding which disrupts the surgeon's view of the treatment site. The $CO_2$ lasers provide a higher rate of ablation and an increased depth of tissue necrosis than their erbium: YAG counterparts. On the other hand, $CO_2$ lasers often create significant residual thermal injury to tissue at and surrounding the treatment site, which requires long healing periods for the patient. In addition, $CO_2$ lasers are associated with much pain and, therefore, require a lot of anesthesia, which increases the cost and length of the procedure.

In the treatment of vascular lesions, lasers are used to irradiate the surface of the skin. The laser energy penetrates through the skin and is absorbed in the blood, which coagulates and collapses the vein. Unfortunately, there are also problems associated with the use of lasers in these procedures. For example, although most of the laser energy passes through the tissue to the vessel, scattering and absorption of the light take place in the tissue. This absorption can cause significant changes in skin coloration and even scarring.

Monopolar electrosurgical instruments have been used to effect electrodessication of abnormalities, such as lesions, skin tags, viral warts, pigment nevi, moles and skin cancer. For example, Conmed Corporation manufacturers a monopolar device, termed the Hyfrecator™ having a single active electrode at the tip of an electrosurgical probe. In these procedures, the skin abnormality is typically removed with a scalpel, and a low voltage is applied to the active electrode in contact with the target tissue to deliver electric current through the tissue and the patient to a dispersive pad or indifferent electrode. The voltage dessicates the remaining abnormal tissue, and coagulates severed blood vessels at the target site. The remaining tissue is then removed with a sponge or similar material. The voltage generally must be low enough to prevent charring and potential scarring of the underlying dermis.

SUMMARY OF THE INVENTION

The present invention provides systems, apparatus and methods for selectively applying electrical energy to structures on the external surface of a patient's body. The systems and methods of the present invention are useful in dermatological procedures, i.e., surface treatment of the patient's outer skin, such as the epidermis and/or the underlying dermis. For example, the present invention is particularly useful for surface tissue ablation on the epidermis and/or collagen shrinkage in the epidermis or dermis, e.g., the removal of pigmentations, vascular lesions (e.g., leg veins), scars, tattoos, etc., and for other surgical procedures on the skin, such as tissue rejuvenation, cosmetic surgery, wrinkle removal, hair removal and/or transplant procedures.

In one aspect of the invention, a method includes positioning one or more electrode terminal(s) on the distal tip of an instrument in close proximity to a target site on an external body surface of the patient. High frequency voltage is applied to the electrode terminal(s) to elevate the temperature of collagen fibers within the tissue at the target site from body temperature (about 37° C.) to a tissue temperature in the range of about 45° C. to 90° C., usually about 60° C. to 70° C., to substantially irreversibly contract these collagen fibers. In a preferred embodiment, an electrically conducting fluid is provided between the electrode terminal (s) and one or more return electrode(s) positioned proximal to the electrode terminal(s) to provide a current flow path from the electrode terminal(s) away from the tissue to the return electrode (s).

The current flow path may be generated by directing an electrically conducting fluid along a fluid path past the return electrode and to the target site, or by locating a viscous electrically conducting fluid, such as a gel, at the target site, and submersing the electrode terminal(s) and the return electrode(s) within the conductive gel. The collagen fibers may be heated either by passing the electric current through the tissue to a selected depth before the current returns to the return electrode(s) and/or by heating the electrically conducting fluid and generating a jet or plume of heated fluid, which is directed towards the target tissue. In the latter embodiment, the electric current may not pass into the tissue at all. In both embodiments, the heated fluid and/or the electric current elevates the temperature of the collagen sufficiently to cause hydrothermal shrinkage of the collagen fibers.

In a specific configuration, the electrode terminal(s) are brought into contact with, or close proximity to, the target tissue so that the electric current passes directly into the tissue to a selected depth. In this embodiment, the return electrode(s) draw the electric current away from the tissue site to limit its depth of penetration into the tissue.

In another aspect of the invention, a high frequency voltage is applied to one or more electrode terminal(s), and a layer of the epidermis is removed from the patient. In some embodiments, the high frequency voltage applied to the electrode terminal(s) creates sufficient heat within the skin to decouple or physically separate the epidermis layer from the underlying papillary dermis. The epidermis layer may then be removed by flushing the treatment site with a fluid, or brushing the epidermis layer away from the treatment site, e.g., with a gauze cloth. In this embodiment, the energy applied to the tissue may be further selected to contract the collagen tissue within the underlying dermis as the epidermis layer is being decoupled or separated therefrom. This method removes the surface layer of the skin, while tightening the underlying dermis to remove wrinkles and rejuvenate the skin.

In other embodiments, the epidermis layer is removed by molecular dissociation or disintegration processes. In these embodiments, the high frequency voltage applied to the electrode terminal(s) is sufficient to vaporize an electrically conductive fluid (e.g., gel or saline) between the electrode terminal(s) and the tissue. Within the vaporized fluid, a ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the plasma layer confines the molecular dissociation process to the surface layer to minimize damage and necrosis to the underlying tissue. This process can be precisely controlled to effect the volumetric removal of tissue as thin as 10 to 50 microns with minimal heating of, or damage to, surrounding or underlying tissue structures. A more complete description of this phenomena is described in commonly assigned U.S. Pat. No. 5,683,366, the complete disclosure of which is incorporated herein by reference.

During the surgical procedure, the electrode terminal(s) will preferably be spaced away from the target tissue by a small distance, e.g., about 0.05 to 5 mm. This spacing allows for the continual resupply of electrically conducting fluid at the interface between the electrode terminal(s) and the target tissue surface. This continual resupply of the electrically conducting fluid helps to ensure that the thin vapor layer or region will remain over at least a portion of the electrode terminal(s) between the electrode terminal(s) and the tissue surface. Preferably, the electrode terminal(s) will be translated and/or rotated transversely relative to the tissue, i.e., in a light brushing motion, to maintain the supply of electrically conducting fluid in the region between the electrode terminal(s) and the tissue. This dynamic movement of the electrode terminal(s) over the tissue site also allows the electrically conducting fluid to cool the tissue surrounding recently removed areas to minimize damage to this surrounding tissue.

In another aspect of the invention, a method of treating an elongated blood vessel in tissue under the surface of the skin is provided. In this method, one or more electrode terminals are positioned in close proximity to the blood vessel, and a sufficient high frequency voltage is applied to the electrode terminal(s) to coagulate blood within the vessel, causing the vessel to collapse. The electrode terminal(s) may be positioned on the external surface of the skin, or they may be introduced through a percutaneous penetration in the outer skin surface to the blood vessel. In the latter embodiment, the percutaneous penetration may be generated with the electrode terminal(s) by applying sufficient energy to the electrode terminal(s) to remove or ablate a portion of the outer skin surface. The electrode terminal(s) are then moved axially through the skin to generate a hole or channel to the blood vessel.

Apparatus according to the present invention generally include an electrosurgical probe or handpiece having a shaft or handle with proximal and distal ends and one or more electrode terminal(s) at the distal end. The apparatus will preferably further include a fluid delivery element for delivering electrically conducting fluid to the electrode terminal (s) and the target site. The fluid delivery element may be located on the probe, e.g., a fluid lumen or tube, or it may be part of a separate instrument. Alternatively, an electrically conducting gel or spray, such as a saline electrolyte or other conductive gel, may be applied the target site. In this embodiment, the apparatus may not have a fluid delivery element. In both embodiments, the electrically conducting fluid will preferably generate a current flow path from the electrode terminals to one or more return electrode(s). In an exemplary embodiment, the return electrode is located on the probe and spaced a sufficient distance from the electrode terminal(s) to substantially avoid or minimize current shorting therebetween and to shield the return electrode from tissue at the target site.

In a specific configuration, the electrosurgical probe will include an electrically insulating electrode support member having a tissue treatment surface at the distal end of the probe. One or more electrode terminals are coupled to, or integral with, the electrode support member. In one embodiment, an electrode array including a plurality of isolated electrode terminals are embedded into the electrode support member such that the electrode terminals are substantially flush with the tissue treatment surface of the electrode support. For superficial removal of a few layers of skin cells, for example, the electrode terminals preferably extend or recede from the support by less than 0.15 mm to limit the ablation rate of underlying cells, thereby allowing the precise removal of thin layers of tissue. In an exemplary embodiment, the electrode terminal(s) have a substantially elongate shape, usually having a width of about 0.01 mm to 2 mm, preferably about 0.1 to 0.5 mm and a length of about 0.5 to 30 mm, preferably about 3 to 7 mm. In this embodiment, the probe is usually traversed along the skin in a direction that is substantially perpendicular to the longitudinal axis of the electrode terminal(s). Applicant has found that this increases the uniformity of treatment on the surface of the skin.

In another aspect of the invention, the electrode support member comprises a plurality of wafer layers bonded together, e.g., by a glass adhesive or the like. The wafer layers each have conductive strips plated or printed thereon to form the electrode terminal(s) and the return electrode(s). In one embodiment, the proximal end of the wafer layers will have a number of holes extending from the conductor strips to an exposed surface of the wafer layers for connection to electrical conductor lead traces in the electrosurgical probe or handpiece. The wafer layers preferably comprise a ceramic material, such as alumina, and the electrode will preferably comprise a metallic material, such as gold, platinum, tungsten, palladium, silver or the like.

In a specific configuration, the electrode support comprises a multilayer ceramic wafer having at least two strips of gold plated on its distal surface and one or more strips of gold plated onto its lateral surfaces. The gold on the distal surface functions as the active electrode terminals, and the gold plated on the lateral surfaces functions as the return electrodes. The active electrode terminals are electrically isolated from each other, and coupled to a lead wire by a gold plated via or hole in the ceramic wafer. The electrode support may have additional electrode terminals plated thereon that function as additional active or return electrodes. In one embodiment, the electrode support includes a pair of outer electrode terminals having a substantially larger surface area than the inner electrode terminals. In this embodiment, the larger, outer electrode terminals serve to heat the tissue so as to provide coagulation of severed blood vessels, or to induce the contraction of collagen fibers in underlying tissue layers, e.g., the dermis, and the inner, small electrode terminals function to remove tissue through molecular dissociation processes.

In another aspect of the invention, an electrosurgical probe comprises a reusable (i.e., sterilizable) handle removably coupled to a disposable tip having an electrode support and one or more electrode terminal(s) thereon. The handle includes a connector for coupling to a high frequency voltage supply and the disposable tip includes an electrical coupling for removably coupling the electrode terminal(s) to the connector. In the preferred embodiment, the probe will further include a fluid delivery element, such as a fluid lumen or tube, having an opening near the electrode terminal (s) for delivering electrically conducting fluid to the electrode terminal(s).

The system may optionally include a temperature controller coupled to one or more temperature sensors at or near the distal end of the probe. The controller adjusts the output voltage of the power supply in response to a temperature set point and the measured temperature value. The temperature sensor may be, for example, a thermocouple, located in the insulating support that measures a temperature at the distal end of the probe. In this embodiment, the temperature set point will preferably be one that corresponds to a tissue temperature that results in the contraction of the collagen tissue, i.e., about 60° C. to 70° C. Alternatively, the temperature sensor may directly measure the tissue temperature (e.g., infrared sensor). This embodiment is advantageous in situations when the surgeon is moving the probe transversely across the tissue.

A further understanding of the nature and advantages of the invention will become apparent by reference to the remaining portions of the specification and drawings.

BRIEF DESCRIPTION OF THE DRAWINGS

FIG. 4 is an end view of the distal tip of the probe, illustrating an electrode support with a plurality of electrode terminals;

FIG. 5 illustrates the electrical connections and the electrode support of the handpiece in greater detail;

FIGS. 9A–12A are side views of the individual wafer layers of the electrode support;

FIGS. 9B–12B are cross-sectional views of the individual wafer layers;

DESCRIPTION OF SPECIFIC EMBODIMENTS

Figure 1:
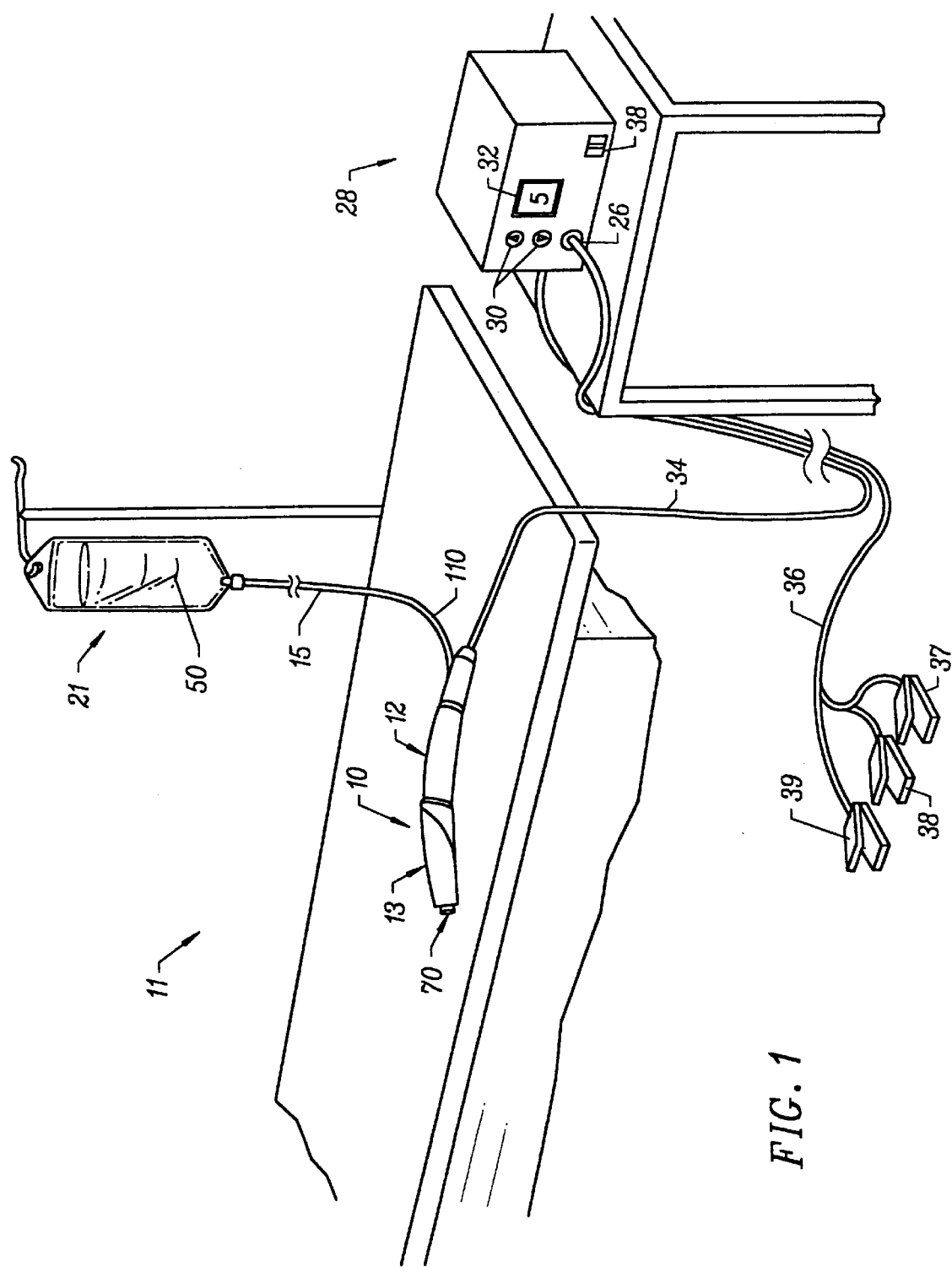
FIG. 1 is a perspective view of an electrosurgical system for treating a patient's skin including an electrosurgical generator and an electrosurgical probe or handpiece.

The present invention provides systems and methods for selectively applying electrical energy to a target location within or on a patient's body, particularly including procedures on an external body surface, such as collagenous tissue within the eye and epidermal and dermal tissues in the skin. For convenience, the remaining disclosure will be directed specifically to skin tissue removal and/or collagen shrinkage in the epidermis or dermis, e.g., the removal of pigmentations, vascular lesions (e.g., leg veins), scars, tattoos, etc., and for other surgical procedures on the skin, such as tissue rejuvenation, cosmetic surgery, wrinkle removal, hair removal and/or transplant procedures. However, it will be appreciated that the system and method can be applied equally well to procedures involving other tissues of the body, as well as to other procedures including open surgery, arthroscopic surgery, laparoscopic surgery, thoracoscopic surgery, and other endoscopic surgical procedures.

The present invention applies high frequency (RF) electrical energy to one or more electrode terminals adjacent an external body surface, such as the outer surface of the skin, to remove and/or modify the structure of tissue structures within the skin. Depending on the specific cosmetic procedure, the present invention may be used to: (1) volumetrically remove tissue or hair (i.e., ablate or effect molecular dissociation of the tissue structure); (2) decouple or separate a tissue layer from an underlying tissue layer so that the tissue layer can later be removed; (3) shrink or contract collagen connective tissue; and/or (4) coagulate blood vessels underlying the surface of the skin.

In some procedures, it is desired to shrink or contract collagen connective tissue within the epidermal and dermal layers of the skin. In these procedures, the RF energy heats the tissue directly by virtue of the electrical current flow therethrough, and/or indirectly through the exposure of the tissue to fluid heated by RF energy, to elevate the tissue temperature from normal body temperatures (e.g., 37° C.) to temperatures in the range of 45° C. to 90° C., preferably in the range from 55° C. to 70° C. Thermal shrinkage of collagen fibers occurs within a small temperature range which, for mammalian collagen is in the range from about 60° C. to 70° C. (Deak, G., et al., "The Thermal Shrinkage Process of Collagen Fibres as Revealed by Polarization Optical Analysis of Topooptical Staining Reactions," Acta Morphologica Acad. Sci. of Hungary, Vol. 15(2), pp 195–208, 1967). Collagen fibers within the skin typically undergo thermal shrinkage in the range of 55° C. to about 62° C. Previously reported research has attributed thermal shrinkage of collagen to the cleaving of the internal stabilizing cross-linkages within the collagen matrix (Deak, ibid). It has also been reported that when the collagen temperature is increased above 70° C., the collagen matrix begins to relax again and the shrinkage effect is reversed resulting in no net shrinkage (Allain, J. C., et al., "Isometric Tensions Developed During the Hydrothermal Swelling of Rat Skin," Connective Tissue Research, Vol. 7, pp 127–133, 1980). Consequently, the controlled heating of tissue to a precise depth is critical to the achievement of therapeutic collagen shrinkage. A more detailed description of collagen shrinkage can be found in U.S. patent application Ser. No. 08/942,580 , filed on Oct. 2, 1997, entitled "SYSTEMS AND METHODS FOR ELECTROSURGICAL TISSUE CONTRACTION".

The preferred depth of heating to effect the shrinkage of collagen in the heated region (i.e., the depth to which the tissue is elevated to temperatures between 55° C. to 70° C.) generally depends on (1) the thickness of the tissue, (2) the location of nearby structures (e.g., nerves) that should not be exposed to damaging temperatures, and/or (3) the location of the collagen tissue layer within which therapeutic shrinkage is to be effected. The depth of heating is usually in the range from 0 to 3.5 mm. In the case of collagen underlying the surface of the skin, the depth of heating is preferably in the range from 0.1 mm to 0.5 mm.

In some procedures (e.g., wrinkle removal, skin tumors, etc.) it may be desired to remove tissue structures on the surface of the skin. In one method of the present invention, a high frequency voltage difference is applied between one or more electrode terminal(s) and one or more return electrode(s) to heat a tissue layer (e.g., the epidermis) sufficiently to decouple or separate the tissue layer from the underlying skin (e.g., the papillary dermis). Once separated, the tissue layer may be physically removed from the patient by a variety of means, such as brushing with a moist cloth or gauze pad, flushing the treatment site, or the like. In this procedure, the voltage difference is preferably sufficient to cause further heating of the underlying skin while the tissue layer is being separated therefrom. This heating, in the exemplary embodiment, will effect contraction of the collagen connective tissue in the underlying skin.

In another method of the present invention, the outer tissue structures are volumetrically removed rather than brushed or flushed away as described above. In this procedure, a high frequency voltage difference is applied between one or more electrode terminal(s) and one or more return electrode(s) to develop high electric field intensities in the vicinity of the target tissue site. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a liquid, such as isotonic saline, delivered to the target site, or a viscous fluid, such as a gel, that is located at the target site. In the latter embodiment, the electrode terminal(s) are submersed in the electrically conductive gel during the surgical procedure. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this phenomena can be found in commonly assigned U.S. Pat. No. 5,683,366 the complete disclosure of which is incorporated herein by reference.

In the above procedure, it may also be desirable to effect collagen shrinkage or contraction of the tissue layers underlying the removed or ablated epidermal tissue. In these procedures, the temperature of the electrode terminal(s) can be carefully controlled such that sufficient thermal energy is transferred to these underlying layers to contract the collagen connective tissue. The thermal energy may be transferred directly through RF current that passes through and resistively heats the underlying tissue layers, or it may be transferred indirectly by heating the electrically conducting fluid, and allowing the heated fluid to contact the underlying layers after the epidermal layers have been removed. A complete description of suitable methods of contracting collagen tissue with RF energy is described in U.S. patent application Ser. No. Unassigned, filed on Oct. 2, 1997, entitled SYSTEMS AND METHODS FOR ELECTROSURGICAL TISSUE CONTRACTION, the complete disclosure of which has previously been incorporated herein by reference.

In other procedures, it may be desired to treat vascular lesions, such as port wine stains, face veins, telangiectasis, birth marks, varicose veins and the like. In these procedures, electrical energy is applied to the vessel such that the energy is absorbed in the blood, which coagulates and collapses the vessel. The blood vessel may be accessed in a variety of manners. For example, high frequency voltage may be applied to one or more electrode terminals at the surface of the skin such that sufficient thermal energy is delivered through the skin to the blood vessel to coagulate the blood therein. Alternatively, the skin may be pierced with the sharpened tip of a probe. In this method, the probe is advanced to a location adjacent to the vessel to be treated, and high frequency energy is applied to the distal end of the probe to coagulate and collapse the vessel at that location. This procedure may be repeated at multiple sites along the length of the vessel so that it will collapse along its length.

In other methods, the high frequency voltage may be focused onto a small spot on the surface of the skin over the vessel to be treated such that a small volume (e.g., channel or hole) of skin is ablated until the vessel is reached. Systems and methods for forming channels or holes through tissue with electrical energy are provided in U.S. Pat. No. 5,683,366.

The present invention may use a single active electrode terminal or an electrode array distributed over a contact surface of a probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the probe to form a single wire that couples to a power source.

The electrosurgical probe will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. For dermatology procedures, the shaft will have any suitable length and diameter that would facilitate handling by the surgeon.

In one configuration, each individual electrode terminal in the electrode array is electrically insulated from all other electrode terminals in the array within said probe and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode may be a tubular member of conductive material proximal to the electrode array at the tip which also serves as a conduit for the supply of the electrically conducting fluid between the active and return electrodes. The application of high frequency voltage between the return electrode and the electrode array results in the generation of high electric field intensities at the distal tips of the electrode terminals with conduction of high frequency current from each individual electrode terminal to the return electrode. The current flow from each individual electrode terminal to the return electrode is controlled by either active or passive means, or a combination thereof, to deliver electrical energy to the surrounding conductive fluid while minimizing energy delivery to surrounding (non-target) tissue.

The application of a high frequency voltage between the return electrode and the electrode array for appropriate time intervals effects heating of the conductive fluid and contraction of the target tissue. The tissue volume over which energy is dissipated (i.e., a high current density exists) may be precisely controlled, for example, by the use of a multiplicity of small electrode terminals whose effective diameters or principal dimensions range from about 10 mm to 0.01 mm, preferably from about 5 mm to 0.05 mm, and more preferably from about 3 mm to 0.1 mm. Electrode areas for both circular and non-circular terminals will have a contact area (per electrode terminal) below 25 $mm^2$, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 75 $mm^2$, preferably from 0.5 $mm^2$ to 40 $mm^2$, and will usually include at least two isolated electrode terminals and preferably about three electrode terminals. Of course, the array may include more than three electrode terminals (e.g., 50 or more electrode terminals) disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The electrode terminal(s) are formed over a tissue treatment surface on the shaft of the electrosurgical probe. The return electrode surface will be recessed relative to the distal end of the probe and may be recessed within a fluid conduit provided for the introduction of electrically conducting fluid to the site of the target tissue and electrode terminal(s).

The area of the tissue treatment surface can vary widely, and the tissue treatment surface can assume a variety of geometries, with particular areas and geometries being selected for specific applications. Active electrode surfaces can have areas in the range from 0.25 mm$^2$ to 75 mm$^2$, usually being from about 0.5 mm$^2$ to 40 mm$^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

In the representative embodiment, the electrode array comprises a plurality of substantially elongate electrode terminals spaced on the contact surface of the shaft. Preferably, the contact surface is an electrically insulating electrode support member extending from the shaft of the probe. The elongate electrode terminals will typically have a length of about 0.5 to 30 mm, preferably about 1 to 15 mm and more preferably about 3 to 7 mm. The width of the elongate electrode terminals is usually about 0.01 to 2 mm, preferably about 0.05 to 1 mm, and more preferably about 0.1 to 0.5 mm. The elongate electrode terminals will be spaced from each other by a distance of about 0.05 to 4 mm, preferably about 0.1 mm to 2 mm. Although the array may comprise one electrode terminal or over 50 electrode terminals, applicant has found that two to ten electrode terminals provides a substantially uniform application of energy to the tissue at the treatment site.

In the exemplary embodiment, the electrode support comprises a plurality of wafer layers bonded together, e.g., by a glass adhesive or the like. The wafer layers each have conductive strips printed thereon to form the electrode terminal(s) and the return electrode(s). In one embodiment, the proximal end of the wafer layers will have a number of holes extending from the conductor strips to an exposed surface of the wafer layers for connection to electrical conductor lead traces in the electrosurgical probe or handpiece. The wafer layers preferably comprise a ceramic material, such as alumina, and the electrode will preferably comprise a metallic material, such as gold, platinum, palladium, tungsten, silver or the like. Suitable multilayer ceramic electrodes are commercially available from e.g., VisPro Corporation of Beaverton, Oreg.

The electrically conducting fluid should have a threshold conductivity to provide a suitable conductive path between the return electrode and the electrode terminal(s). The electrical conductivity of the fluid (in units of milliSiemens per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. Alternatively, the fluid may be an electrically conductive gel or spray, such as a saline electrolyte gel, a conductive ECG spray, an electrode conductivity gel, an ultrasound transmission or scanning gel, or the like. Suitable gels or sprays are commercially available from Graham-Field, Inc of Hauppauge, N.Y.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer between the electrode terminal(s) and the tissue at the treatment site throughout the procedure, which reduces the thermal damage that might otherwise occur if the vapor layer were extinguished due to a lack of conductive fluid. The electrically conductive fluid also helps maintain the tissue temperature as low as possible during the procedure.

The voltage applied between the return electrode and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation or ablation). Typically, the peak-to-peak voltage will be in the range of 10 to 2000 volts and preferably in the range of 20 to 1200 volts and more preferably in the range of about 40 to 800 volts (again, depending on the electrode size, the operating frequency and the operation mode).

Figure 21:
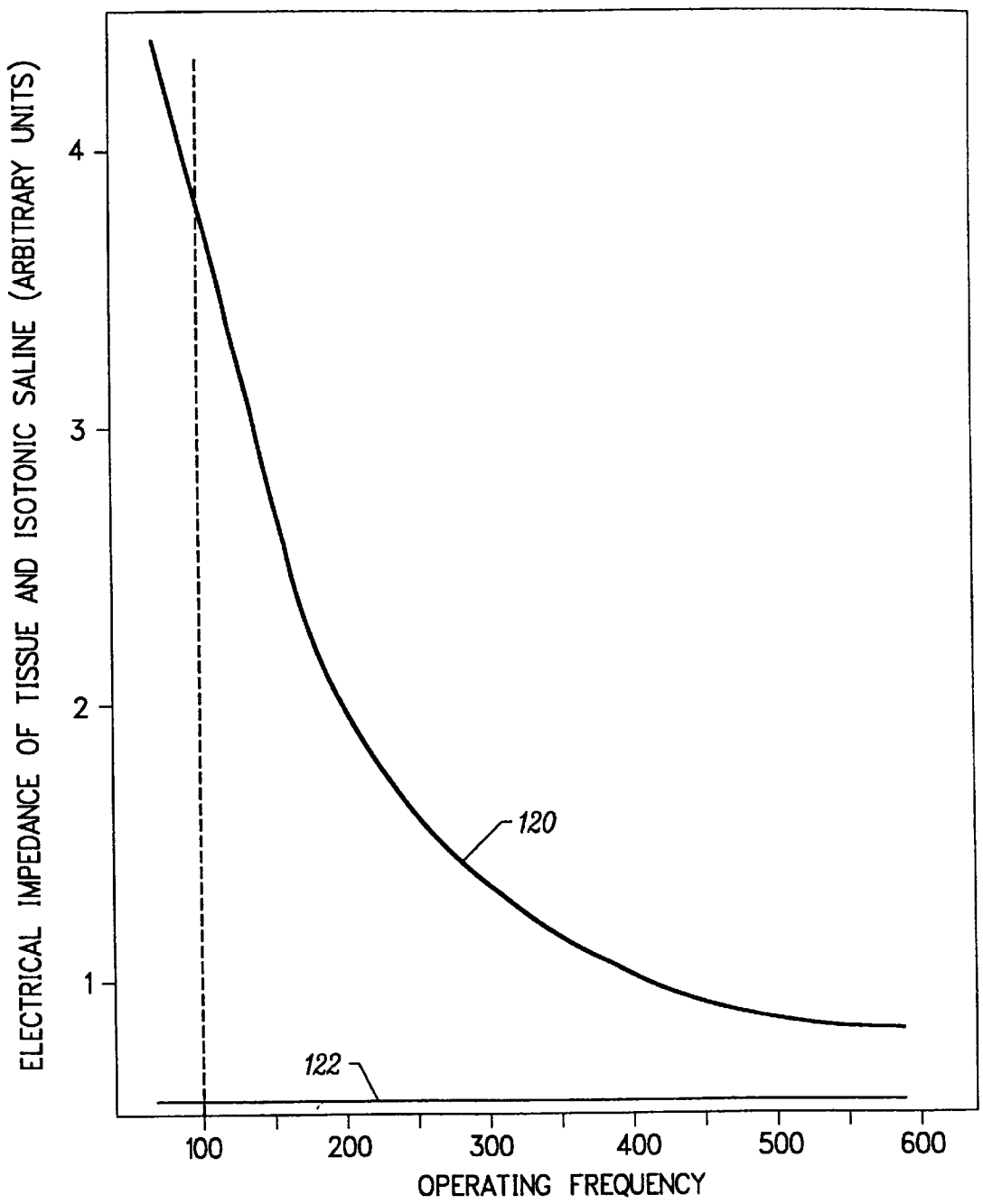
FIG. 21 is a graph illustrating the electrical impedance of tissue and isotonic saline with operating frequency.

An important aspect of the present invention is the discovery that the frequency of the output voltage of the generator can be selected to control the depth of tissue heating. Referring to FIG. 21, the electrical impedance of tissue is known to decrease with increasing frequency due to the electrical properties of cell membranes which surround electrically conductive cellular fluid. As shown, the electrical impedance of tissue to current at a frequency of 100 kHz is on the order of four times larger than at a frequency of 450 to 500 kHz. As a result of the higher tissue impedance, the current flux lines tend to penetrate less deeply resulting in a smaller depth of tissue heating. This principle of operation of the present invention can be used to advantage in applications where the depth of tissue heating is to be maintained small (e.g., 0.2 to 0.5 mm). Preferably, the operating frequency should be below 350 kHz for applications requiring shallow depths of tissue heating (e.g., less than 1.5 mm). Conversely, in situations where much larger depths of tissue heating are to be effected, a higher output voltage frequency may be used. By way of example, to achieve therapeutic collagen shrinkage to a depth of 1.5 to 3.0 mm, a higher operating frequency may be used (e.g., 500 kHz).

Alternatively, the diameter of the electrode terminals and/or the spacing between the outer perimeter of the electrode terminals and the electrode support member may be selected to increase the depth of current penetration. By way of example, increasing the distance between the outer perimeter of the support member and the electrode terminals will increase the depth of heating for a given operating frequency.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, the total number of electrode(s) and/or the maximum allowed temperature selected for the probe tip. The power source allows the user to select the voltage level according to the specific requirements of a particular arthroscopic surgery, cosmetic surgery, dermatological procedure, ophthalmic procedures, open surgery or other endoscopic surgery procedure. A description of a suitable power source can be found in "SYSTEMS AND METHODS FOR ELECTROSURGICAL TISSUE AND FLUID COAGULATION", filed on Oct. 23, 1997 Ser. No. 60/062,997, the complete disclosure of which has been previously incorporated herein by reference.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the size of the electrode terminal(s), the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source.

During the surgical procedure, the distal end of the probe or the electrode terminal(s) will be maintained at a small distance away from the target tissue surface. This small spacing allows for the continual resupply of electrically conducting fluid into the interface between the electrode terminal(s) and the target tissue surface. This continual resupply of the electrically conducting fluid helps to ensure that the thin vapor layer will remain between electrode terminal(s) and the tissue surface. In addition, dynamic movement of the electrode terminal(s) over the tissue site allows the electrically conducting fluid to cool the tissue underlying and surrounding the target tissue to minimize thermal damage to this surrounding and underlying tissue. To that end, the electrically conducting fluid may be cooled to facilitate this cooling of the tissue. Typically, the active electrode(s) will be about 0.02 to 2 mm from the target tissue and preferably about 0.05 to 0.5 mm during the ablation process. One method of maintaining this space is to translate and/or rotate the probe transversely relative to the tissue, i.e., a light brushing motion, to maintain a thin vaporized layer or region between the active electrode and the tissue. Of course, if coagulation or collagen shrinkage of a deeper region of tissue is necessary (e.g., for sealing a bleeding vessel imbedded within the tissue), it may be desirable to press the electrode terminal(s) against the tissue to effect joulean heating therein.

Referring to FIG. 1, an electrosurgical system 11 generally comprises an electrosurgical handpiece or probe 10 connected to a power supply 28 for providing high frequency voltage to a target site and a fluid source 21 for supplying electrically conducting fluid 50 to probe 10. Probe 10 generally includes a proximal handle 12 and a distal tip 13 having an electrode support member 70 with one or an array of electrode terminals 58 and one or more return electrodes 100, 102 (see FIGS. 2, 4 and 5) disposed on the support member 70. A connecting cable 34 has a connector 26 for electrically coupling the electrodes in probe 10 to power supply 28. The electrode terminals 58 are electrically isolated from each other and each of the terminals 58 is connected to an active or passive control network within power supply 28 by means of a plurality of individually insulated conductors (not shown). A fluid supply tube 15 is connected to a fluid tube 110 of probe 10 for supplying electrically conducting fluid 50 to the distal tip 13 (see FIGS. 16 and 17).

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjusting the energy level applied to electrode terminals 58. In an exemplary embodiment, first foot pedal 37 is used to place the power supply into the "ablation" mode and second foot pedal 38 places power supply 28 into the "coagulation" mode. The third foot pedal 39 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing the vapor layer and accelerating these charged particles against the tissue). As discussed above, the requisite voltage level for ablation will vary depending on the number, size, shape and spacing of the electrodes, the distance in which the electrodes extend from the support member, etc. When the surgeon is using the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 28 applies a low enough voltage to one or more electrode terminals (or one or more coagulation electrodes) to avoid vaporization of the electrically conductive fluid, formation of a plasma and subsequent molecular dissociation of the tissue. The surgeon may automatically toggle the power supply between the ablation and coagulation modes by alternatively stepping on foot pedals 37, 38, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulate small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37. A specific design of a suitable power supply for use with the present invention can be found in provisional patent application entitled "SYSTEMS AND METHODS FOR ELECTROSURGICAL TISSUE AND FLUID COAGULATION", filed Oct. 23, 1997 Ser. No. 60/062, 997.

Figure 2:
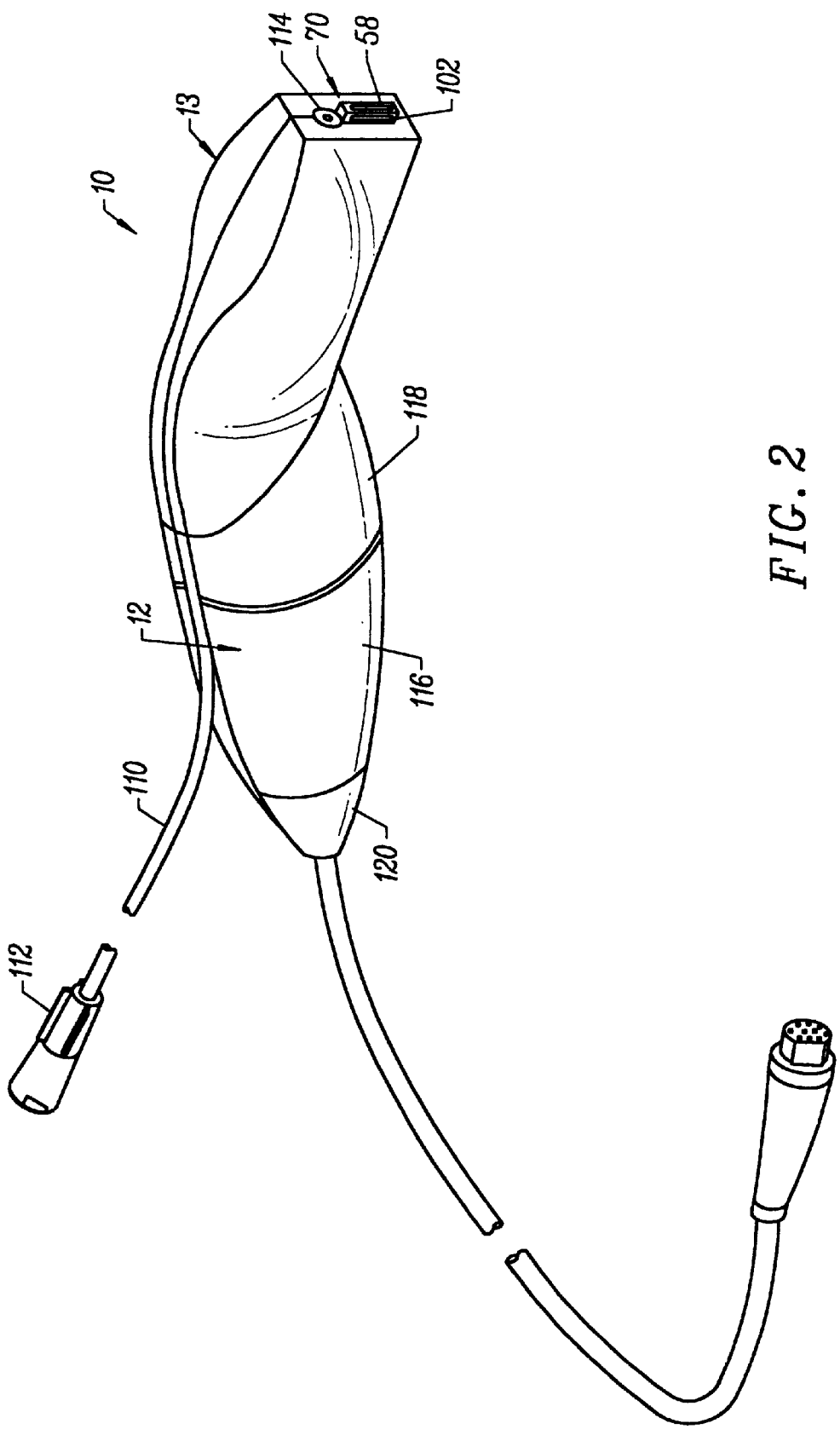
FIG. 2 is a perspective view of one embodiment of an electrosurgical probe constructed according to the principles of the present invention.

Referring now to FIGS. 2–5, an exemplary electrosurgical probe 10 comprises a shaft or disposable tip 13 removably coupled to a proximal handle 12, and an electrically insulating electrode support member 70 extending from tip 13 for supporting a plurality of electrode terminals 58 (see FIGS. 2 and 5). Tip 13 and handle 12 typically comprise a plastic material that is easily molded into a suitable shape for handling by the surgeon. As shown in FIGS. 3 and 5, handle 12 defines an inner cavity 72 that houses the electrical connections 74 (discussed below in reference to FIG. 5), and provides a suitable interface for connection to electrical connecting cable 34 (see FIG. 1). In the exemplary embodiment, handle 12 is constructed of a steam autoclavable plastic or metal (e.g., polyethylether keytone, or a stable metal alloy containing aluminum and/or zinc. so that it can be re-used by sterilizing handle 12 between surgical procedures. High service temperature materials are preferred, such as a silicone cable jacket and a poly-ether-imide handpiece or ULTEM® that can withstand a repeated exposure to high temperatures.

Figure 3A:
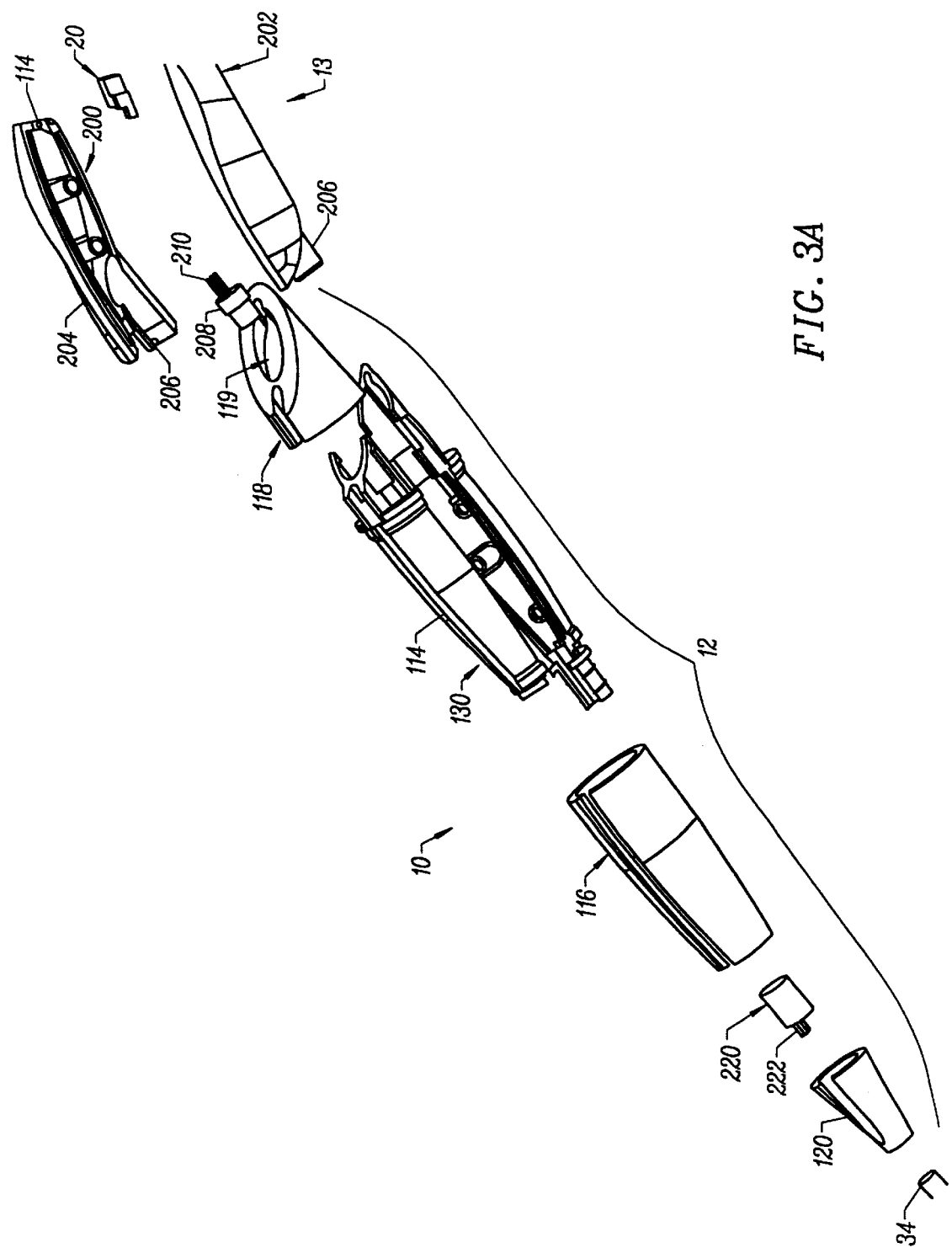
FIGS. 3A–3C are exploded, isometric views of the probe of FIG. 2.
Figure 3B:
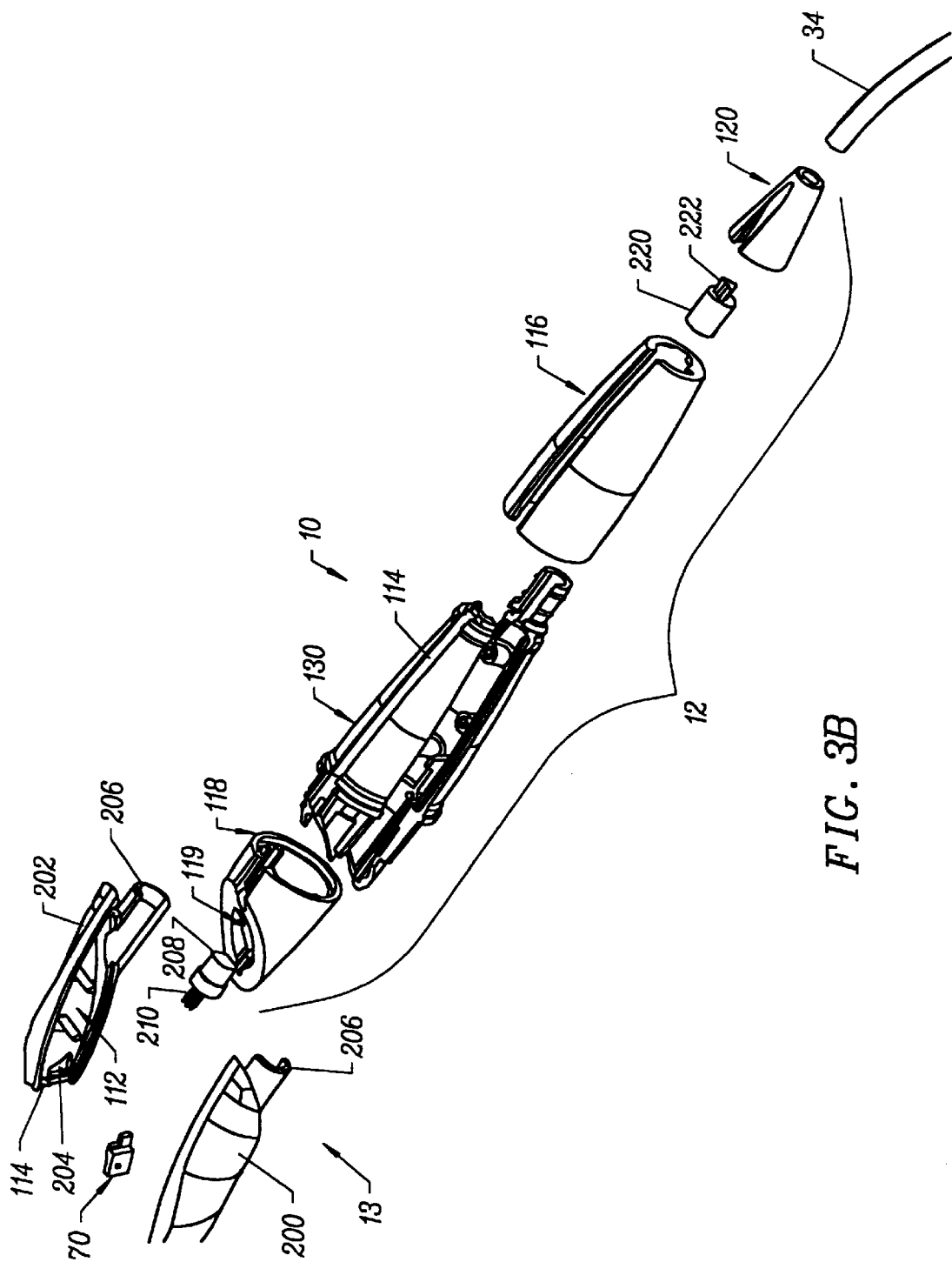
Figure 3C:
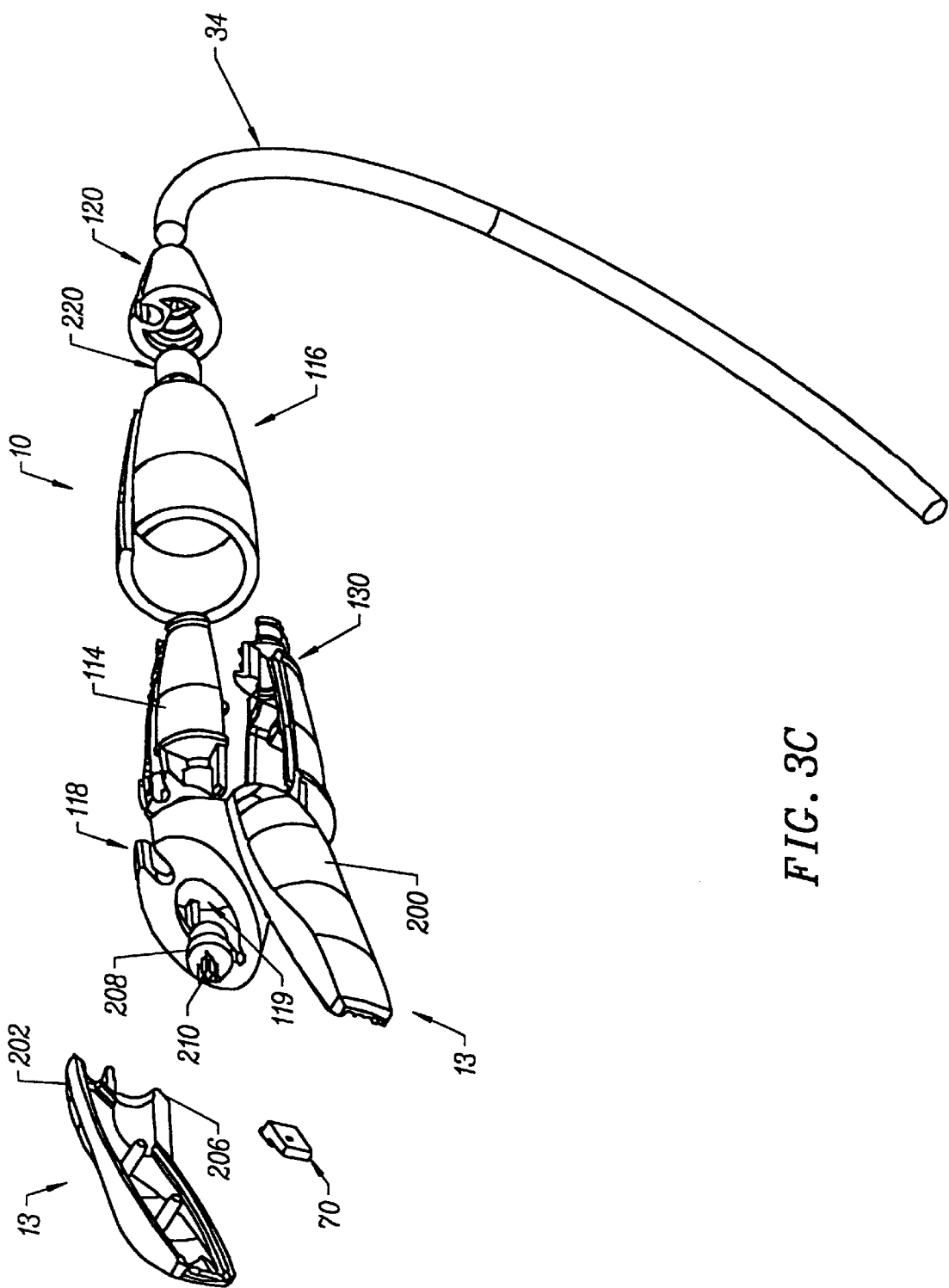
Figure 6:
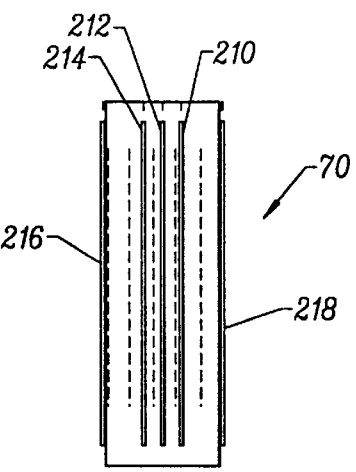
FIG. 6 is an end view of an exemplary electrode support comprising a multilayer wafer with plated conductors for electrodes.

Referring to FIGS. 3A–3C, tip 13 preferably comprises first and second housing halves 200, 202 that snap fit together, and form a recess 204 therebetween for holding electrode support member 70 within the tip 13. Electrode support member 70 extends from the distal end of tip 13 (usually about 0.5 to 20 mm), and provides support for a plurality of electrically isolated electrode terminals 58 and one or more return electrodes 100, 102 (see FIG. 4). Alternatively, electrode support member 70 may be recessed from the distal end of tip 13 to help confine the electrically conductive fluid around the electrode terminals 58 during the surgical procedure, as discussed above. Electrode support member 70 has a substantially planar tissue treatment surface 80 that is usually disposed at an angle of about 10 to 90 degrees relative to the longitudinal axis of handle 12 to facilitate handling by the surgeon. In the exemplary embodiment, this function is accomplished by orienting tip 13 at an acute angle relative to the longitudinal axis of handle 12.

In the embodiment shown in FIGS. 2–5, probe 10 includes first and second return electrodes 100, 102 for completing the current path between electrode terminals 58 and power supply 28 (see FIG. 1). As shown, return electrodes 100, 102 preferably have fluid contact surfaces on either lateral surface 104, 106 of electrode support member 70 slightly proximal to tissue treatment surface 80, typically about 0.1 to 2 mm, preferably about 0.2 to 1 mm. Return electrodes 100, 102 will usually have an exposed surface area of about 5 $mm^2$ to 25 $mm^2$, preferably about 18 $mm^2$ to about 20 $mm^2$. Return electrodes 100, 102 are coupled to a connector 104 (details of this connection discussed below) that extends to the proximal end of handle 13, where it is suitably connected to power supply 28 (FIG. 1).

Referring to FIGS. 4A–4C and FIG. 5, tip 13 further includes a proximal hub 206 for supporting a male electrical connector 208 that holds a plurality of wires 210 each coupled to one of the electrode terminals 58 and the return electrodes 100, 102 on support member 70 (see FIGS. 7–13 for details of the representative support member 70). A female connector 220 housed within handle 12 is removably coupled to male connector 208, and a plurality of wires 222 extend from female connector 220 through a strain relief 224 to cable 34. Both sets of wires 210, 222 are insulated to prevent shorting in the event of fluid ingress into the probe 10. This design allows for removable connection of the electrodes in tip 13 with the connector 220 within handle 12 so that the handle can be re-used with different tips 13. Probe 10 will preferably also include an identification element, such as a coded resistor (not shown), for programming a particular voltage output range and mode of operation for the power supply. This allows the power supply to be employed with a variety of different probes for a variety of different applications.

As shown in FIG. 5, return electrodes 100, 102 are not directly connected to electrode terminals 58. To complete this current path so that electrode terminals 58 are electrically connected to return electrodes 102, 100, electrically conducting fluid (e.g., isotonic saline or electrically conducting gel) is located between the active and return electrodes during a surgical procedure. In the representative embodiment, probe 10 includes a fluid tube 110 (FIG. 2) for delivering electrically conductive fluid to the target site. Fluid tube 110 is sized to extend through a groove 114 in handle 13 and through an inner cavity 112 (FIG. 3 and FIGS. 4A–4C) in tip 12 to a distal opening 114 (FIG. 4) located adjacent electrode support member 70. Tube 110 extends all the way through inner cavity 112 to opening 114 to eliminate any possible fluid ingress into cavity 112. As shown in FIGS. 1 and 2, fluid tube 110 includes a proximal connector 112 for coupling to an electrically conductive fluid source 21.

Probe 10 will also include a valve or equivalent structure for controlling the flow rate of the electrically conducting fluid to the target site. In the representative embodiment shown in FIGS. 4A–4C, handle 12 comprises a main body 130 coupled between distal hub 118 and strain relief 120, and a rotatable sleeve 116 around main body 130. Distal hub 118 has an opening 119 for receiving proximal hub 206 of tip 13 for removably coupling the tip 13 to the handle 12. Sleeve 116 is rotatably coupled to strain relief 120 and distal hub 118 to provide a valve structure for fluid tube 110. As shown in FIG. 2, fluid tube 110 extends through groove 114 from strain relief 120, through main body 130 and distal hub 120 to tip 13. Rotation of sleeve 116 will impede, and eventually obstruct, the flow of fluid through tube 110. Of course, this fluid control may be provided by a variety of other input and valve devices, such as switches, buttons, etc.

In alternative embodiments, the fluid path may be directly formed in probe 10 by, for example, a central inner lumen or an annular gap (not shown) within the handle and the tip. This inner lumen may be formed near the perimeter of the probe 10 such that the electrically conducting fluid tends to flow radially inward towards the target site, or it may be formed towards the center of probe 10 so that the fluid flows radially outward. In addition, the electrically conducting fluid may be delivered from a fluid delivery element (not shown) that is separate from probe 10. In arthroscopic surgery, for example, the body cavity will be flooded with isotonic saline and the probe 10 will be introduced into this flooded cavity. Electrically conducting fluid will be continually resupplied to maintain the conduction path between return electrodes 100, 102 and electrode terminals 58. A more complete description of alternative electrosurgical probes incorporating one or more fluid lumen(s) can be found in commonly assigned, co-pending application Ser. No. 08/485,219, filed on Jun. 7, 1995, the complete disclosure of which has previously been incorporated herein by reference.

Referring to FIGS. 4 and 5, electrically isolated electrode terminals 58 are spaced apart over tissue treatment surface 80 of electrode support member 70. In the representative embodiment, the tissue treatment surface 80 has a rectangular cross-sectional shape with a length L in the range of about 0.5 mm to 20 mm (preferably about 2 to 10 mm) and a width W in the range from 0.3 mm to 10 mm (preferably about 0.5 to 4 mm). The individual electrode terminals 58 have the dimensions described above, and are preferably substantially flush with tissue treatment surface 80. Applicant has found that this configuration minimizes any sharp electrode edges and/or corners that would promote excessively high electric field intensities and associated current densities when a high frequency voltage is applied to the electrode terminals, thereby minimizing the rate of ablation as preferred for removing thin layers of tissue (e.g., epidermal layers).

It should be noted that the electrode terminals 58 may protrude slightly outward from surface 80, typically by a distance from 0 mm to 2 mm, or the terminals may be recessed from this surface. For example, the electrode terminals 58 may be recessed by a distance from 0.01 mm to 1 mm, preferably 0.01 mm to 0.2 mm. In one embodiment of the invention, the electrode terminals are axially adjustable relative to the tissue treatment surface so that the surgeon can adjust the distance between the surface and the electrode terminals.

Referring now to FIGS. 7–13, an exemplary electrode support member 70 will be described in detail. As shown, electrode support member 70 preferably comprises a multilayer substrate comprising a suitable high temperature, electrically insulating material, such as ceramic. The multilayer substrate is a thin or thick-film hybrid having conductive strips that are adhered to the ceramic wafer layers (e.g., thick-film printed and fired onto or plated onto the ceramic wafers). The conductive strips typically comprise tungsten, gold, nickel, silver, platinum or equivalent materials. In the exemplary embodiment, the conductive strips comprise gold, and they are co-fired together with the wafer layers to form an integral package. The conductive strips are coupled to external wire connectors by holes or vias that are drilled through the ceramic layers, and plated or otherwise covered with conductive material.

Figures 7, 8:
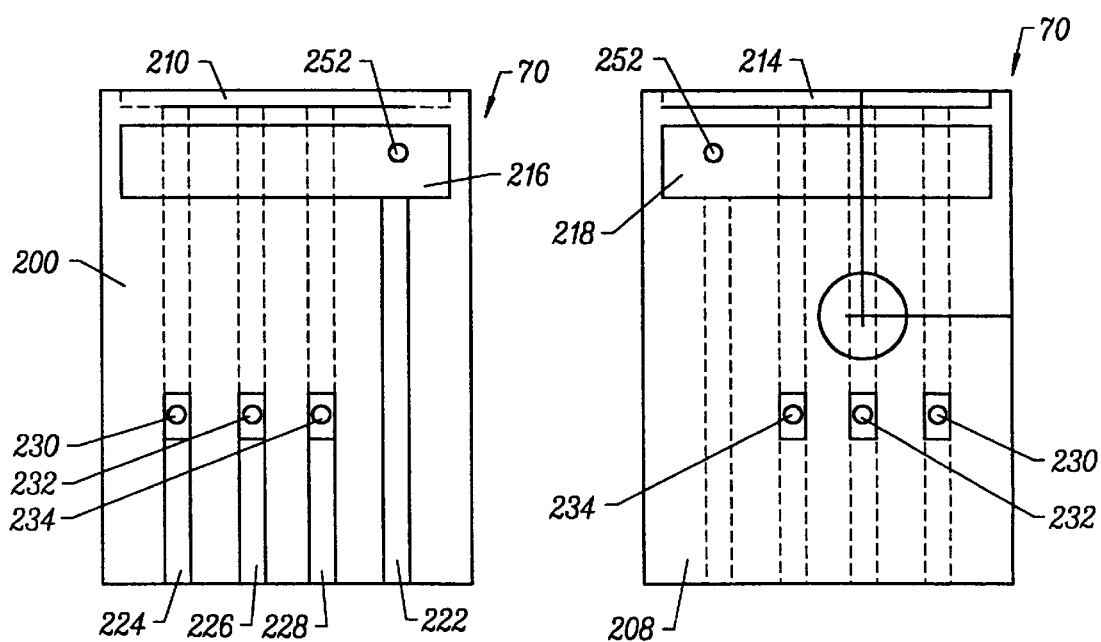
FIGS. 7 and 8 are side views of the electrode support of FIG. 7.

In the representative embodiment, support member 70 comprises five ceramic layers 200, 202, 204, 206, 208 (see FIGS. 9–13), three gold plated electrode terminals 210, 212, 214 and first and second gold plated return electrodes 216, 218. As shown in FIGS. 8, 9A and 9B, a first ceramic layer 200, which is one of the outer layers of support 70, includes first gold plated return electrode 216 on a lateral surface 220 thereof. First ceramic layer 200 further includes a gold conductive strip 222 extending from return electrode 216 to the proximal end of the layer 200 for coupling to a lead wire (not shown), and three gold conductive lines 224, 226, 228 extending from a mid-portion of the layer 200 to its proximal end. Conductive strips 224, 226, 228 are each coupled to one of the electrode terminals 210, 212, 214 by conductive holes or vias 230, 232, 234, respectively. As shown, all three vias 230, 232, 234 extend through wafer layer 200.

Figure 13:
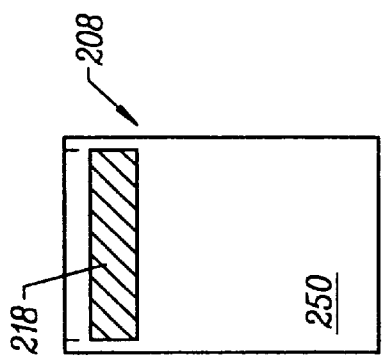
FIG. 13 is a side view of an individual wafer layer.
Figure 12A:
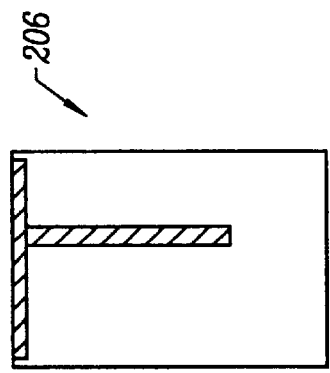
Figure 12B:
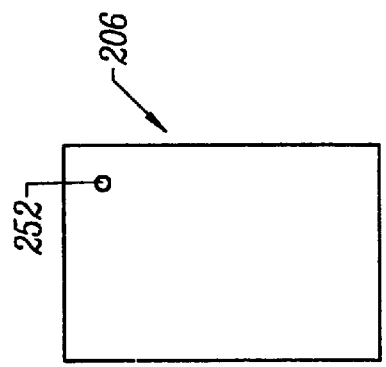
Figure 11A:
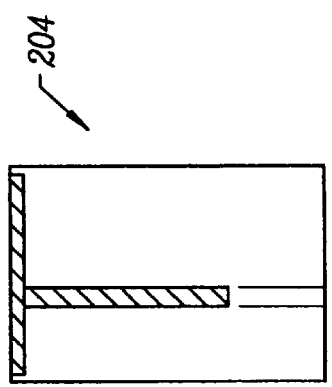
Figure 11B:
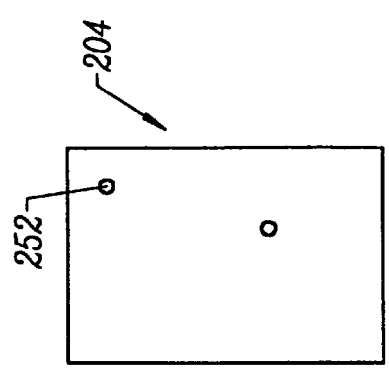

Referring to FIGS. 10A and 10B, a second wafer layer 202 is bonded between the outer wafer layer 200 and a middle wafer layer 204 (FIGS. 11A and 11B). As shown, first electrode terminal 210 is attached to the distal surface of second wafer layer 202, and a conductive strip 240 extends to via 230 to couple electrode terminal 210 to a lead wire. Similarly, wafer layers 204 and 206 (FIGS. 11 and 12) each have an electrode terminal 212, 214 plated to their distal surfaces, and a conductive strip 242, 244, respectively, extending to one of the vias 232, 234, respectively. Note that the vias only extend as far as necessary through the ceramic layers. As shown in FIG. 13, another outer wafer layer 208 has a second return electrode 218 plated to the lateral surface 250 of layer 208. The second return electrode 218 is coupled directly to the first return electrode 216 through a via 252 extending through the entire ceramic substrate.

Figure 14:
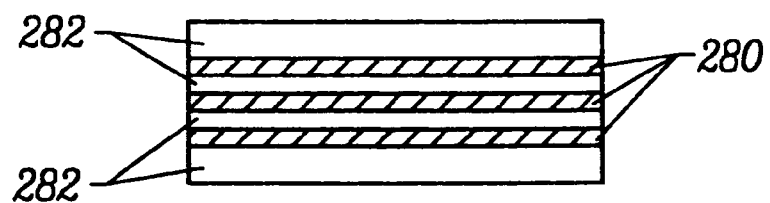
FIGS. 14 and 15 illustrate an alternative multi-layer wafer design according to the present invention.
Figure 15:
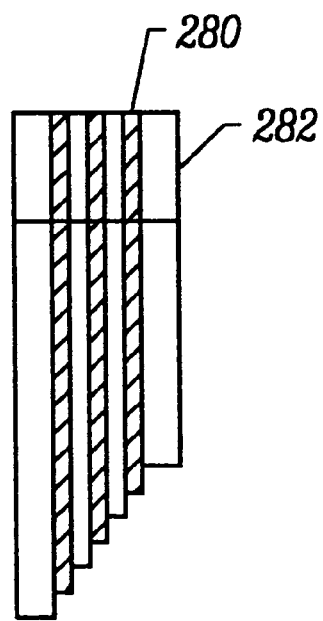

Of course, it will be recognized that a variety of different types of multilayer wafers may be constructed according to the present invention, For example, FIGS. 14 and 15 illustrate an alternative embodiment of the multilayer ceramic wafer, wherein the electrode terminals comprise planar strips 280 that are plated or otherwise bonded between the ceramic wafer layers 282. Each of the planar strips 280 has a different length, as shown in FIG. 15, so that the electrode terminals can be electrically isolated from each other, and coupled to lead wires by vias (not shown).

Figure 16A:
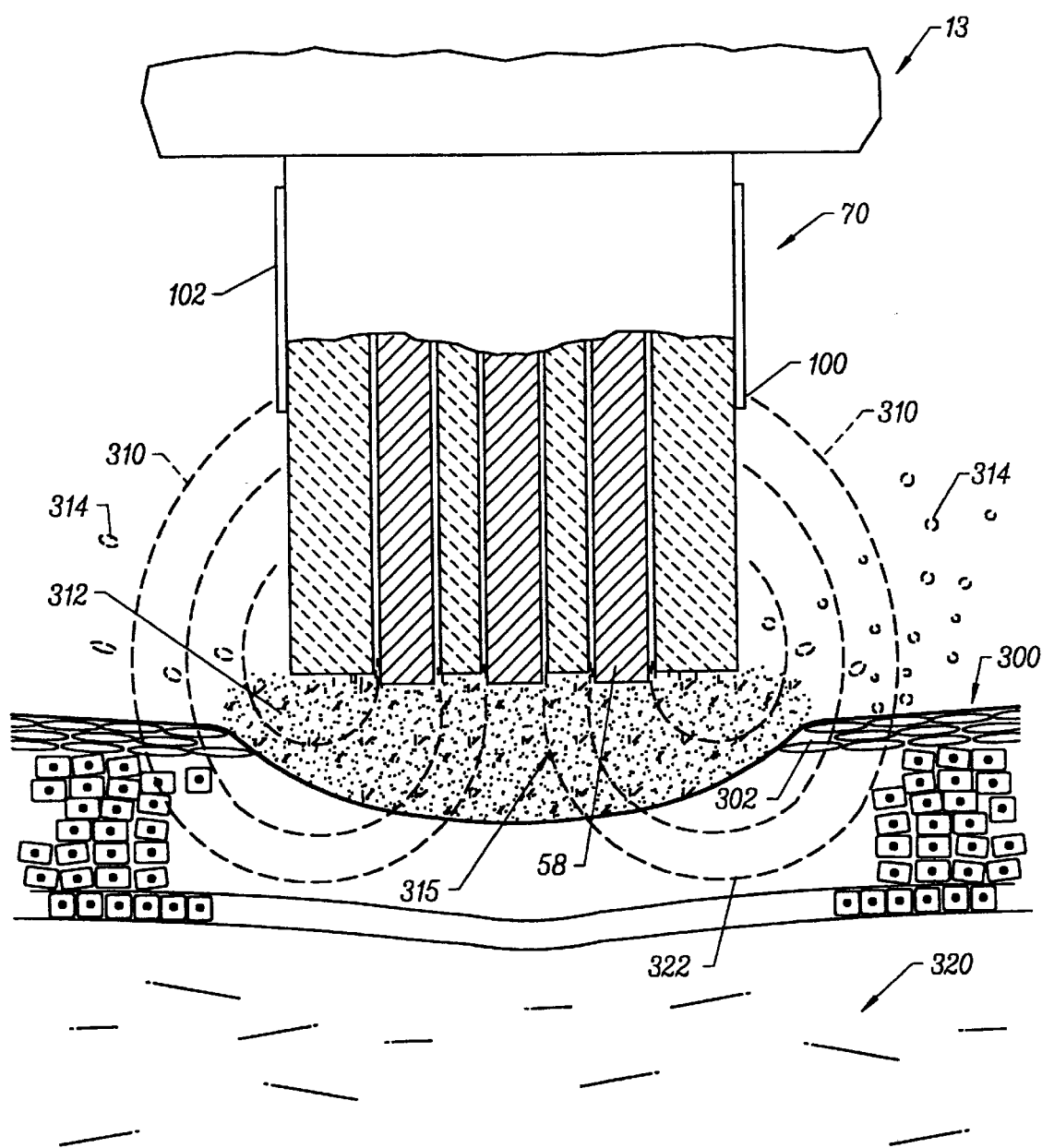
FIG. 16A illustrates a method for treating the outer layer of a patient's skin in a skin resurfacing procedure, wherein an outer layer of epidermis is removed or ablated and the collagen fibers in the underlying dermis are contracted.
Figure 16B:
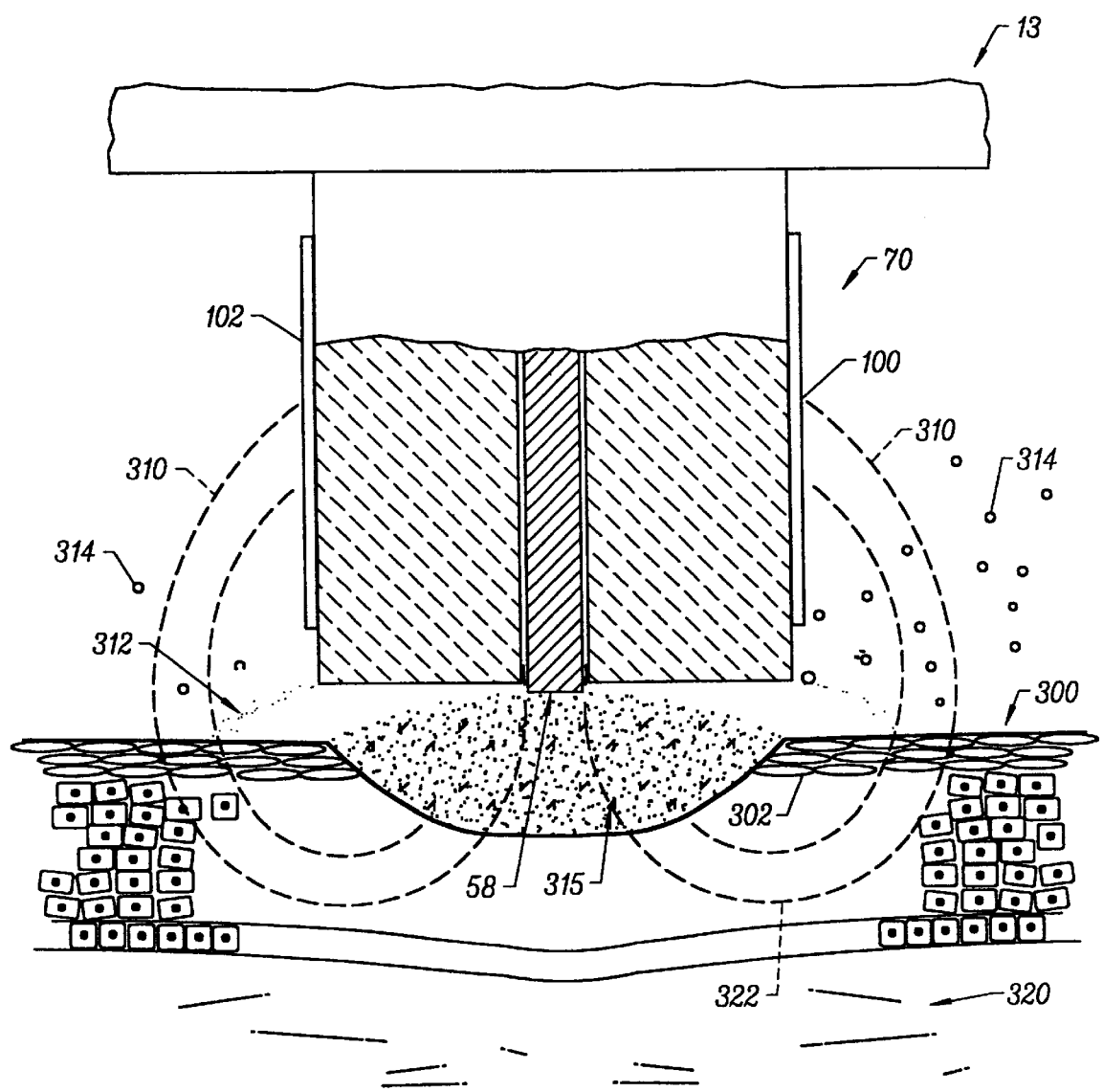
FIG. 16B illustrates a illustrates a method for treating the outer layer of a patient's skin in a skin resurfacing procedure with an electrosurgical probe having a single, active electrode terminal.

Referring now to FIGS. 16A and 16B, a method of treating tissue on the outer skin of a patient according to the present invention will now be described. As shown, distal tip 13 of probe 10 is positioned such that electrode support 70 is adjacent to the target tissue 302 at the treatment site 300. Electrically conducting fluid 304 is delivered through fluid tube 110 (FIG. 2) through distal hole 114 to the treatment site 300. The rate of fluid flow is controlled with rotatable sleeve 116 (FIG. 4A) such that the zone between the tissue 302 and electrode support 70 is constantly immersed in the fluid. The power supply 28 is then turned on and adjusted such that a high frequency voltage difference is applied between electrode terminal(s) 58 and return electrodes 100, 102. The electrically conducting fluid 304 provides the conduction path (see current flux lines 310) between electrode terminal(s) 58 and the return electrodes 100, 102 on either side of electrode support 70.

In the exemplary embodiment, the high frequency voltage is sufficient to convert the electrically conductive fluid 304 between the target tissue 302 and electrode terminals 58 into an ionized vapor layer 312 or plasma. As a result of the applied voltage difference between electrode terminals 58 and the target tissue 302 (i.e., the voltage gradient across the plasma layer 312), charged particles 315 in the plasma (viz., electrons) are accelerated towards the tissue. At sufficiently high voltage differences, these charged particles 315 gain sufficient energy to cause dissociation of the molecular bonds within tissue structures. This molecular dissociation is accompanied by the volumetric removal (i.e, ablative sublimation) of tissue and the production of low molecular weight gases 314, such as oxygen, nitrogen, carbon dioxide, hydrogen and methane. The short range of the accelerated charged particles 315 within the target tissue 302 confines the molecular dissociation process to the surface layer to minimize damage and necrosis to the underlying tissue 320.

In some embodiments, the voltage difference will be sufficient enough to apply thermal energy to the underlying tissue 320. Preferably, this thermal energy will be sufficient to elevate the tissue temperature from normal body temperatures (e.g., 37° C.) to temperatures in the range of 45° C. to 90° C., preferably in the range from 55° C. to 70° C. and, for the case of skin, preferably in the range of about 55° C. to 62° C. This temperature elevation causes contraction of the collagen connective fibers within the underlying tissue 320. This method removes the surface layer of the skin, while tightening the underlying dermis to remove wrinkles and rejuvenate the skin.

Figure 17:
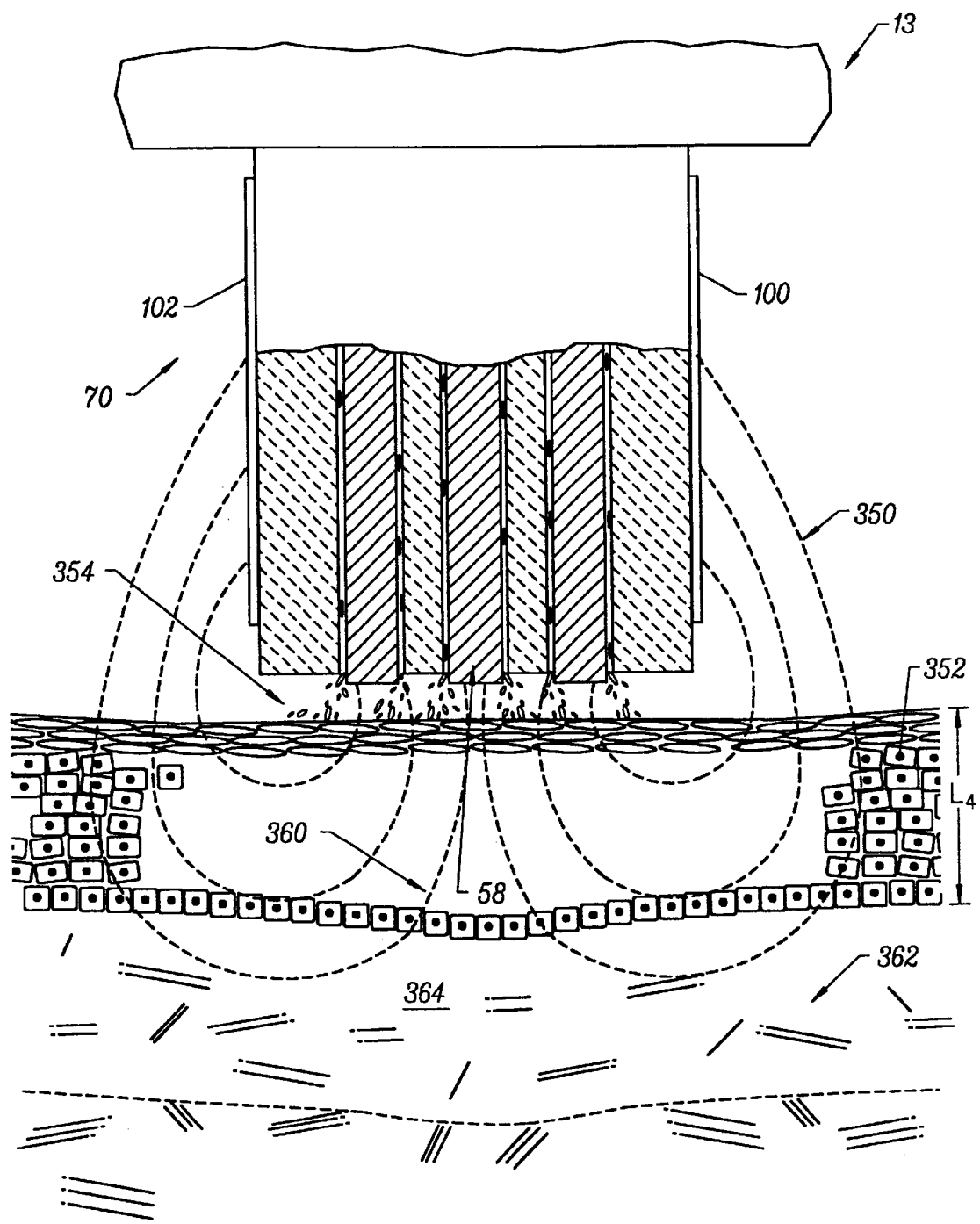
FIG. 17 illustrates a method of skin resurfacing wherein the epidermal layer is separated from the papillary dermis, and then removed by wiping away the separated layer.

An alternative method for skin rejuvenation or wrinkle removal is shown in FIG. 17. In this method, when a voltage difference is applied between the electrode terminals 58 and the return electrodes 100, 102, electrical current flows between the electrode terminals 58 and the return electrode 100, 102 along current flux lines 350. The current flux lines 350 flow a short distance, $L_4$ into the surface of epidermal tissue 352 and through the electrically conductive fluid 354 in the region above the surface of the tissue to complete the electrical path between the electrode terminals 58 and the return electrodes 100, 102. As a consequence of the electrical impedance of the tissue and the proper selection of the applied frequency, voltage and current, heating of the epidermal tissue 352 occurs in a region 360 below the surface of the tissue 352. This heating elevates the temperature of the tissue and separates the epidermal tissue layer 352 from the underlying papillary dermis 362. The epidermal tissue layer 352 may then be removed by flushing the treatment site, or by brushing away this tissue layer 352 with, for example, a cloth pad, gauze, etc. In skin rejuvenation procedures, collagen may be injected into the dermis after the epidermis has been removed to rejuvenate skin that has lost its elasticity.

In addition, the heating from current flux lines 350 may be sufficient to elevate the temperature of the tissue 364 in the papillary dermis 362 from normal body temperature (e.g. 37° C.) to a temperature in the range 55° C. to 85° C., preferably in the range from 60° C. to 70° C. This heating of the papillary dermis 362 will cause irreversible contraction of the collagen with the papillary dermis.

Figure 18A:
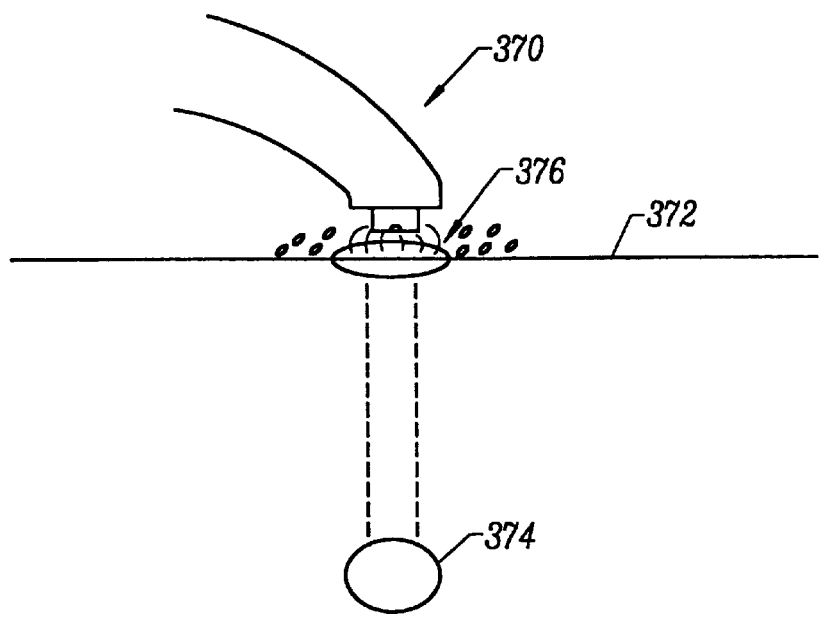
FIGS. 18A and 18B illustrate a method for treating a vascular lesion.
Figure 18B:
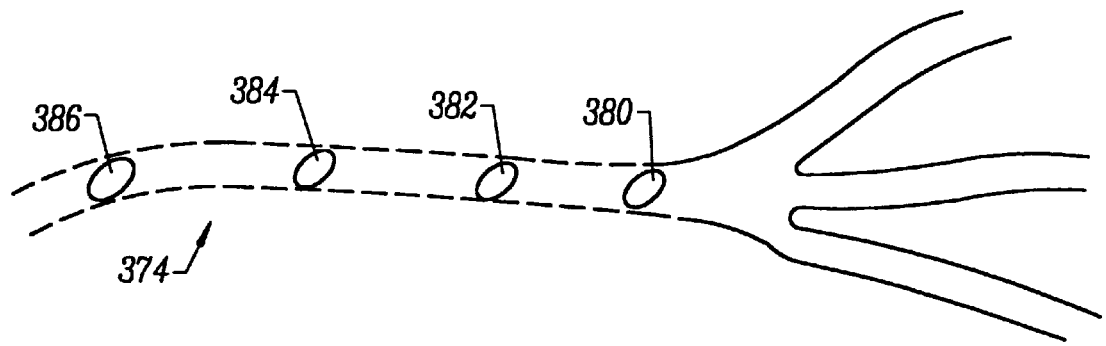

FIGS. 18A and 18B illustrate a method for treating a vascular lesion, such as a port wine stain, face vein, birth mark or the like. As shown in FIG. 18A, an electrosurgical probe 370 is placed on or adjacent to the surface of the skin 372 above the vessel 374 to be treated. A voltage difference is applied between the active and return electrodes (not shown) in the presence of electrically conductive fluid 376 to ablate or cause molecular dissociation of the tissue adjacent the probe 370. As the tissue is removed, the probe will be axially translated through the deepening hole to the vessel 374 (note that a substantially linear probe shaft is preferred in this embodiment). A more complete description of systems and methods for forming channels or holes through tissue is described in commonly assigned, U.S. Pat. No. 5,683,366, the complete disclosure of which is incorporated herein by reference. Once the probe approaches the vessel, thermal energy will be delivered into the vessel from the current flux lines as described above. This thermal energy will eventually be sufficient to coagulate the blood in the vessel 374 and collapse the vessel at that site.

In order to collapse a long length of the vessel 374, multiple treatment sites may be necessary. As shown in FIG. 18B, it is desirable to locate the first treatment site 380 at a downstream point with respect to the flow of blood in the vessel. The surgeon may then sequentially treat the vessel at multiple sites (382, 384, 386) upstream from the first site 380.

Figure 19:
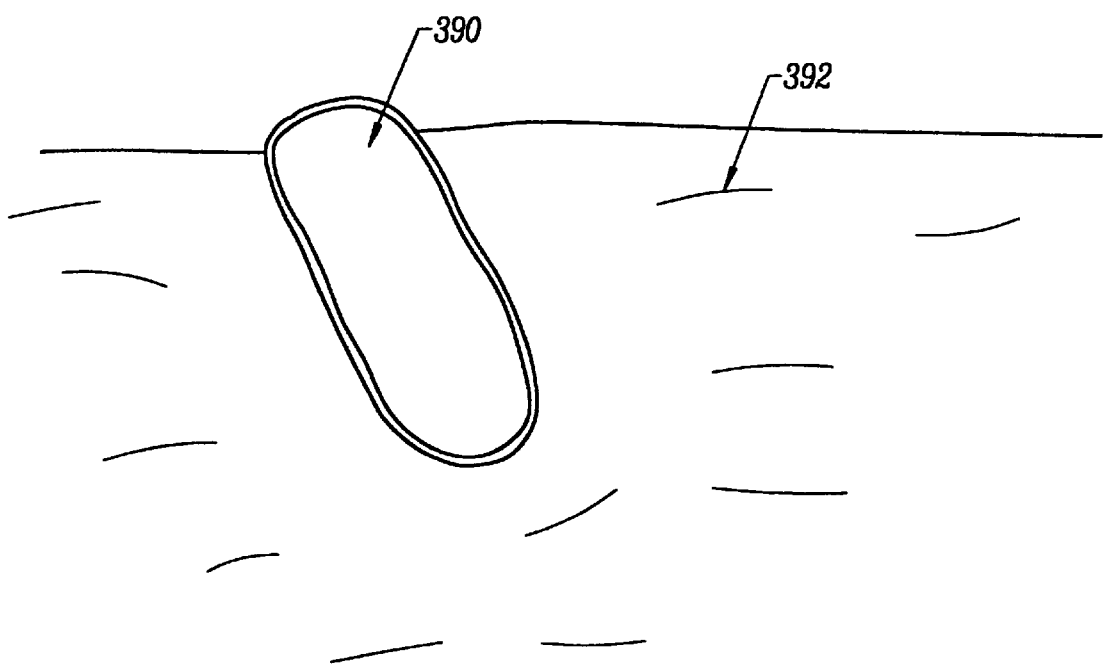
FIG. 19 illustrates a method of removing scalp tissue and/or hair according to the present invention.

Referring now to FIG. 19, a method for transplanting hair according to the present invention is described. A strip of hair (not shown) from a donor region is first excised from the patient. The hair may be excised by removing the tissue around the strip in a similar manner as described above. The hemostatic effects of the electrosurgical system of the present invention result in minimal bleeding at the donor site. The strip is then lifted from the scalp and sutures are used to close the opening.

One of the probes described above are then used to produce incisions 390 in the recipient area 392. As shown in FIG. 19, the depth an diameter of the incision 390 can be accurately controlled. The incisions are preferably formed at an angle to improve the retention of the graft and to form a more cosmetically suitable appearance.

Figure 20:
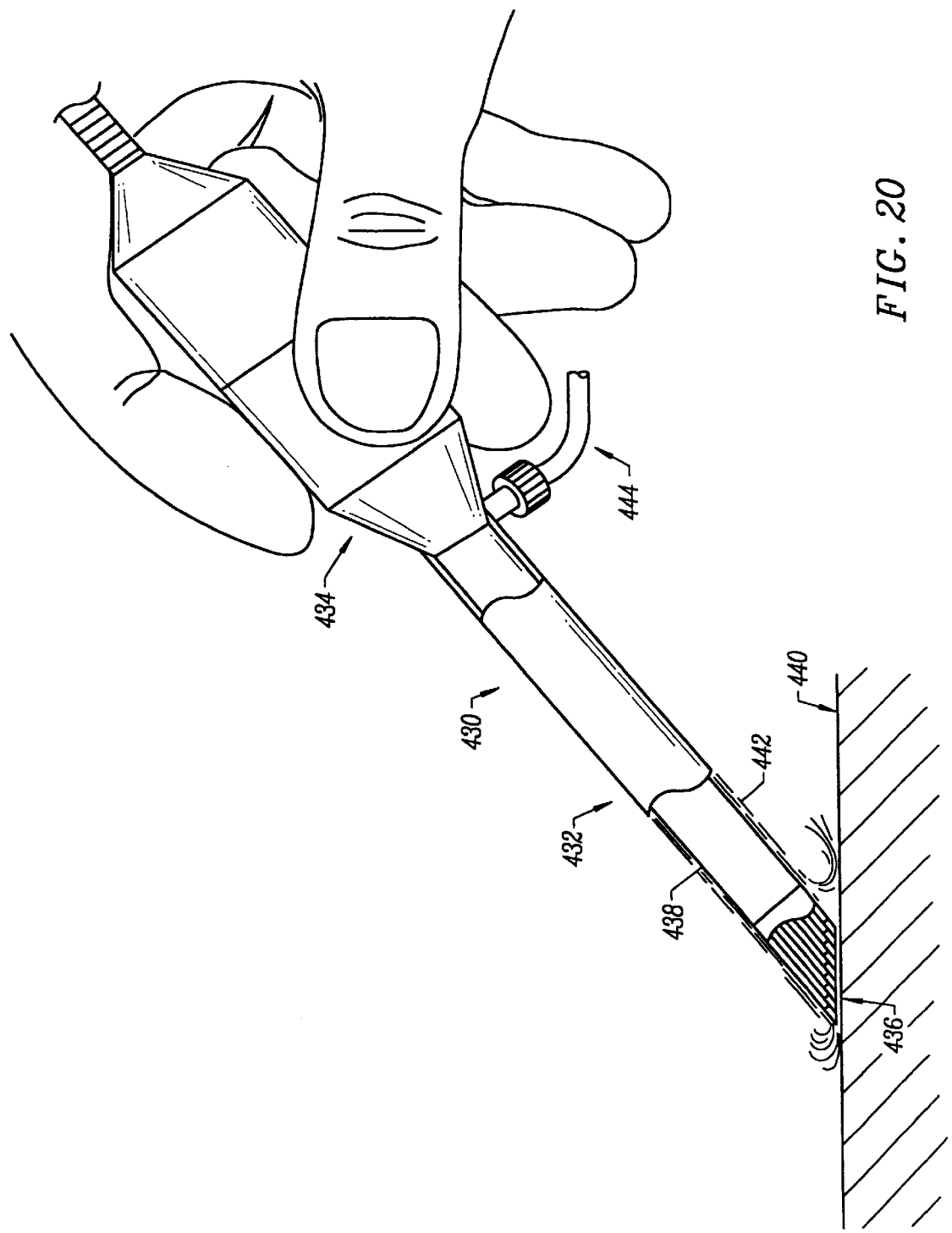
FIG. 20 is a cross-sectional view of an alternative electrosurgical probe for applying high frequency voltage to tissue layers on the skin.

FIG. 20 illustrates an alternative embodiment, where an electrosurgical probe 430 is utilized to remove the surface layers of the epidermis 440. Probe 430 includes a shaft 432 coupled to a proximal handle 434 for holding and controlling shaft 432. Similar to previous embodiments, probe 430 includes an active electrode array 436 at the distal tip of shaft 432, an annular return electrode 438 extending through shaft 432 and proximally recessed from the active electrode array 436 and an annular lumen 442 between return electrode 438 and an outer insulating sheath 444. Probe 430 further includes a liquid supply conduit 446 attached to handle 434 and in fluid communication with lumen 442 and a source of electrically conducting fluid (not shown) for delivering the fluid past return electrode 438 to the target site on the epidermis 440. As discussed above, electrode array 436 is preferably flush with the distal end of shaft 432 or distally extended from the distal end by a small distance (on the order of 0.005 inches) so to minimize the depth of ablation. Preferably, the distal end of shaft 432 is beveled to improve access and control of probe 430 while treating the epidermal tissue.

Figure 22:
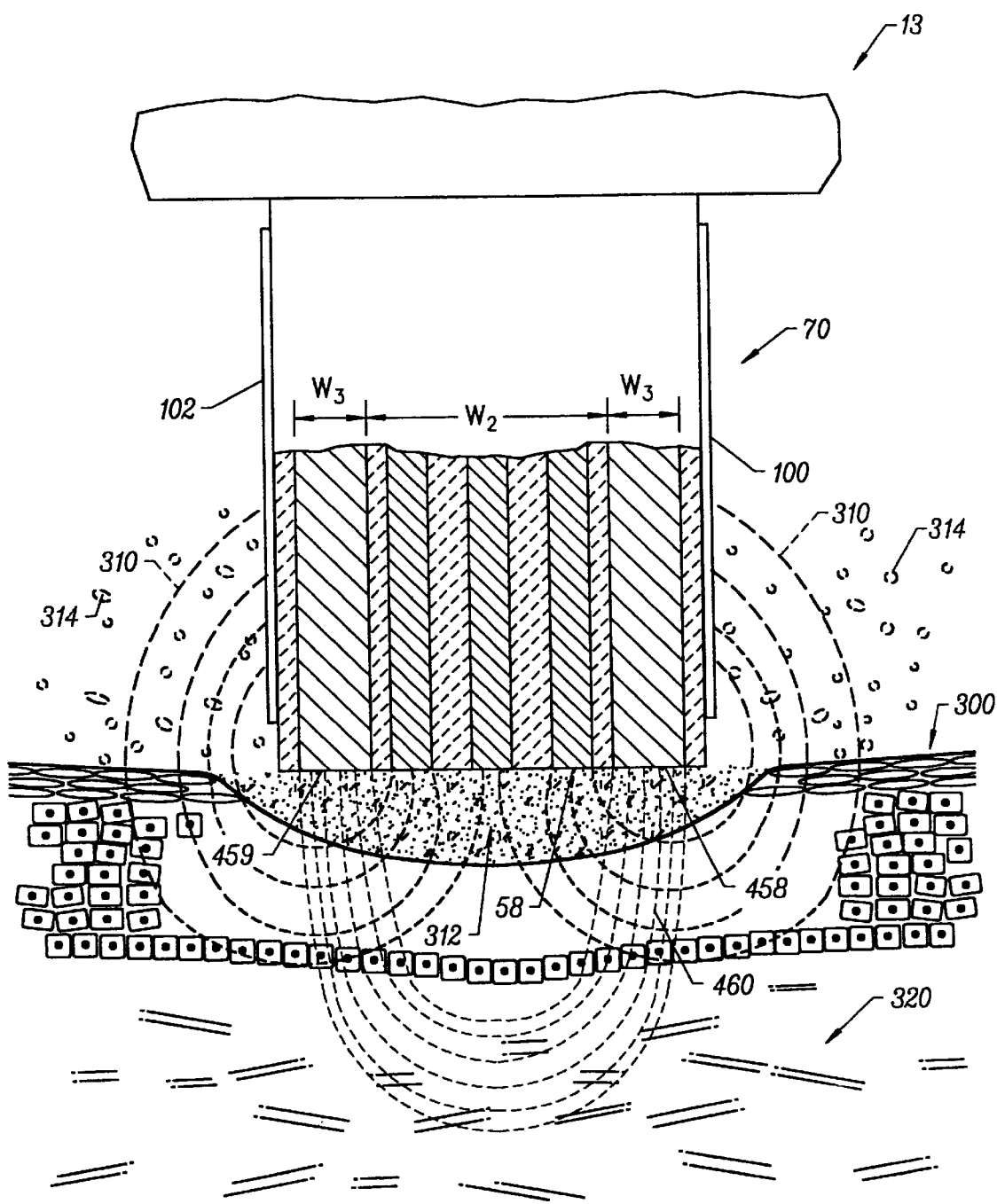
FIG. 22 illustrates another embodiment of the probe of the present invention, incorporating additional electrodes sized for contraction of tissue.

Yet another embodiment of the present invention is shown in FIG. 22. This embodiment is similar to that shown in FIG. 16 and described above with the exception that additional electrode terminals 458, 459 are positioned at the distal tip 70 of the probe. Electrode terminals 458, 459 may be the same size as ablation electrode terminals 58, larger as shown in FIG. 22. One operating arrangement is to connect electrode terminals 458, 459 to two poles of a high frequency generator to form a bipolar circuit allowing current to flow between terminals 458, 459 as shown by current flux lines 460. The electrode terminals 458, 459 are electrically isolated from ablation electrodes 58. By proper selection of the interelectrode spaing, $W_2$, and electrode width, $W_3$, and the frequency, the current flux lines 460 can be caused to flow below the epidermis layer to effect collagen shrinkage in region 320 as described hereinabove.

The voltage will preferably be sufficient to establish high electric field intensities between the active electrode array 436 and the epidermal tissue 440 to thereby induce molecular breakdown or disintegration of several cell layers of the epidermal tissue. As described above, a sufficient voltage will be applied to develop a thin layer of vapor within the electrically conducting fluid and to ionize the vaporized layer or region between the active electrode(s) and the target tissue. Energy in the form of photons and/or energetic electrons are discharged from the vapor layer to ablate the epidermal tissue, thereby minimizing necrosis of surrounding tissue and underlying cell layers, such as cell structures in the stratum lucidium and/or stratum granulosum.

The system and method of the present invention may also be useful to efficaciously ablate (i.e., disintegrate) cancer cells and tissue containing cancer cells, such as cancer on the surface of the epidermis, eye, colon, bladder, cervix, uterus and the like. The present invention's ability to completely disintegrate the target tissue can be advantageous in this application because simply vaporizing and fragmenting cancerous tissue may lead to spreading of viable cancer cells (i.e., seeding) to other portions of the patient's body or to the surgical team in close proximity to the target tissue. In addition, the cancerous tissue can be removed to a precise depth while minimizing necrosis of the underlying tissue.

Other modifications and variations can be made to disclose embodiments without departing from the subject invention as defined in the following claims. For example, it should be noted that the invention is not limited to an electrode array comprising a plurality of electrode terminals. The invention could utilize a plurality of return electrodes, e.g., in a bipolar array or the like. In addition, depending on other conditions, such as the peak-to-peak voltage, electrode diameter, etc., a single electrode terminal may be sufficient to contract collagen tissue, ablate tissue, or the like.

Further, the electrode array may include both active and return electrodes. In this embodiment, the active and return electrodes are both located on a distal tissue treatment surface adjacent to each other. The active and return electrodes may be located in active/return electrode pairs, or one or more return electrodes may be located on the distal tip together with a plurality of electrically isolated electrode terminals. The proximal return electrode may or may not be employed in the embodiments that incorporate return electrodes at the distal tip of the probe. For example, if it is desired to maintain the current flux lines around the distal tip of the probe, the proximal return electrode will not be desired.

What is claimed is:

1. A method for treatment of an external body surface comprising:
   positioning an electrode terminal in close proximity to a target site on an external body surface of a patient; and
   applying high frequency electrical energy to the electrode terminal, the electrical energy being sufficient to remove a layer of the external body surface and to effect contraction of collagen fibers within tissue underlying the layer.

2. The method of claim 1 wherein the layer comprises a tissue structure in the epidermis.

3. The method of claim 1 wherein the collagen fibers are heated to a temperature in the range of about 45° C. to 90° C.

4. The method of claim 1 wherein the collagen fibers are heated to a temperature in the range of about 55° C. to about 70° C.

5. The method of claim 1 further comprising delivering electrically conductive fluid to the target site, and contacting the electrically conductive fluid with a return electrode to provide a current flow path from the electrode terminal, through the electrically conductive fluid, and to the return electrode.

6. The method of claim 5 further comprising positioning the return electrode proximal to the electrode terminal to induce current flow from the electrode terminal away from the target site.

7. The method of claim 5 further comprising directing the electrically conductive fluid along a fluid path past the electrode terminal and the return electrode to generate the current flow path between the return electrode and the electrode terminal.

8. The method of claim 5 wherein the high frequency electrical energy is high frequency voltage, the method further comprising applying sufficient high frequency voltage to the electrode terminal to vaporize at least a portion of the electrically conductive fluid between the electrode terminal and the external body surface.

9. The method of claim 8 further comprising applying sufficient high frequency voltage to the electrode terminal to ionize the vaporized portion of the electrically conductive fluid to generate a plasma layer between the electrode terminal and the external body surface.

10. The method of claim 1 wherein the electrode terminal comprises an electrode array including a plurality of electrically isolated electrode terminals.

11. The method of claim 10 further comprising independently controlling current flow from at least two of the electrode terminals based on impedance between the electrode terminal and a return electrode.

12. The method of claim 1 further comprising supporting the electrode terminal with an electrosurgical probe having a tissue treatment surface near a distal end of the probe, wherein the electrode terminal is substantially flush with the tissue treatment surface.

13. The method of claim 1 wherein the electrical energy is sufficient to induce a contraction of collagen fibers at the target site without causing dissociation or molecular breakdown of the collagen fibers.

14. The method of claim 1 further comprising controlling a depth of tissue penetration of the electrical energy into the tissue to control a depth of thermal heating of said tissue.

15. The method of claim 14 wherein the controlling step is carried out by controlling a frequency of the electrical energy applied to the electrode terminal and a return electrode.

16. The method of claim 1 wherein the electrical energy has a frequency of less than 350 kHz.

17. The method of claim 1 wherein the electrical energy has a frequency of about 100 to 200 kHz.

18. The method of claim 1 wherein the tissue underlying the layer of external body surface comprises a tissue structure in the dermis.

19. The method of claim 1 further comprising locating an electrically conductive gel on the external body surface to provide a current flow path from the electrode terminal, through the electrically conductive gel, and to a return electrode.

20. The method of claim 1 wherein the electrical energy is sufficient to ablate the layer of the external body surface.

21. The method of claim 20 wherein the layer of the external body surface is removed through molecular dissociation or disintegration.

22. A method of resurfacing a portion of a patient's skin comprising:

positioning an active electrode adjacent to, or in contact with, an epidermis surface at a target site on a patient's skin in the presence of electrically conductive fluid;

positioning a return electrode in the electrically conductive fluid to generate a current path between the active and return electrodes through the electrically conductive fluid;

applying a high frequency voltage between the active and return electrodes, the voltage being sufficient to heat collagen fibers within the dermis to a range of about 45° C. to about 90° C.: and removing a portion of the epidermis surface during the applying step.

23. The method of claim 22 wherein, during the applying step, electric current passes from the active electrode along the current path to the return electrode without penetrating the epidermis surface.

24. The method of claim 22 wherein, during the applying step, electric current passes from the active electrode into the patient's skin and along conductive path to the return electrode.

25. The method of claim 22 wherein the collagen fibers are heated to a temperature in the range of about 55° C. to about 70° C.

26. The method of claim 22 further comprising delivering the electrically conductive fluid to the target site through an electrosurgical instrument, the instrument comprising the active and return electrodes.

27. The method of claim 22 further comprising positioning the return electrode proximal to the active electrode to induce current flow from the active electrode away from the target site.

28. The method of claim 22 wherein the active electrode comprises an electrode array including a plurality of electrically isolated electrode terminals.

29. The method of claim 22 further comprising supporting the active electrode with an electrosurgical probe having a tissue treatment surface near a distal end of the probe, wherein the active electrode is substantially flush with the tissue treatment surface.

30. The method of claim 22 further comprising controlling a depth of tissue penetration of electric current into the tissue to control a depth of thermal heating of said tissue.

31. The method of claim 30 wherein the controlling step is carried out by controlling a frequency of the voltage applied between the active and return electrodes, wherein the voltage has a frequency of less than 350 kHz.

32. The method of claim 31 wherein the voltage has a frequency of about 100 to 200 kHz.

33. A method of resurfacing a portion of a patient's skin comprising:

positioning an active electrode adjacent to, or in contact with, an epidermis surface at a target site on a patient's skin in the presence of electrically conductive fluid;

positioning a return electrode in the electrically conductive fluid to generate a current path between the active and return electrodes through the electrically conductive fluid;

positioning the return electrode proximal to the active electrode to induce current flow from the active electrode away from the target site; and applying a high frequency voltage between the active and return electrodes, the voltage being sufficient to heat collagen fibers within the dermis to a range of about 45° C. to about 90° C.

34. The method of claim 33 wherein, during the applying step, electric current passes from the active electrode along the current path to the return electrode without penetrating the epidermis surface.

35. The method of claim 33 wherein, during the applying step, electric current passes from the active electrode into the patient's skin and along a conductive path to the return electrode.

36. The method of claim 33 further comprising removing a portion of the epidermis surface during the applying step.

37. The method of claim 33 wherein the collagen fibers are heated to a temperature in the range of about 55° C. to about 70° C.

38. The method of claim 33 further comprising delivering the electrically conductive fluid to the target site through an electrosurgical instrument, the instrument comprising the active and return electrodes.

39. The method of claim 33 wherein the active electrode comprises an electrode array including a plurality of electrically isolated electrode terminals.

40. The method of claim 33 further comprising supporting the active electrode with an electrosurgical probe having a tissue treatment surface near a distal end of the probe, wherein the active electrode is substantially flush with the tissue treatment surface.

41. The method of claim 33 further comprising controlling a depth of tissue penetration of electric current into the tissue to control a depth of thermal heating of said tissue.

42. The method of claim 41 wherein the controlling step is carried out by controlling a frequency of the voltage applied between the active and return electrodes, wherein the voltage has a frequency of less than 350 kHz.

43. The method of claim 42 wherein the voltage has a frequency of about 100 to 200 kHz.

* * * * *